(12) United States Patent
Dreher et al.

(10) Patent No.: US 11,337,501 B2
(45) Date of Patent: May 24, 2022

(54) HAIR COLOR CARTRIDGE AND COMPOSITIONS FOR USE IN THE HAIR COLOR CARTRIDGE

(71) Applicant: L'OREAL, Paris (FR)

(72) Inventors: Kimberly Dreher, Brielle, NJ (US); Jeremy Puco, West Caldwell, NJ (US); Caroline Goget, Summit, NJ (US)

(73) Assignee: L'OREAL, Paris (FR)

(*) Notice: Subject to any disclaimer, the term of this patent is extended or adjusted under 35 U.S.C. 154(b) by 0 days.

(21) Appl. No.: 17/169,881

(22) Filed: Feb. 8, 2021

(65) Prior Publication Data

US 2021/0177118 A1 Jun. 17, 2021

Related U.S. Application Data

(63) Continuation of application No. 15/850,828, filed on Dec. 21, 2017, now Pat. No. 10,918,183.

(51) Int. Cl.
*A61Q 5/10* (2006.01)
*A45D 19/02* (2006.01)
(Continued)

(52) U.S. Cl.
CPC ............ *A45D 19/02* (2013.01); *A45D 34/042* (2013.01); *A46B 9/023* (2013.01); *A46B 11/002* (2013.01);
(Continued)

(58) Field of Classification Search
CPC . A61Q 5/10; A61K 8/22; A61K 8/411; A61K 8/415; A61K 8/4926; A61K 8/41;
(Continued)

(56) References Cited

U.S. PATENT DOCUMENTS 5,393,305 A * 2/1995 Cohen .................. A61Q 5/10
8/406
7,243,660 B2 7/2007 Capristo
(Continued)

FOREIGN PATENT DOCUMENTS

| EP | 3015099 A1 | 5/2016 |
| WO | 2003070183 A2 | 8/2003 |
| WO | 2013160257 A2 | 10/2013 |

OTHER PUBLICATIONS

International Search Report and Written Opinion dated Mar. 28, 2019 for corresponding PCT Application No. PCT/US2018/064475.

*Primary Examiner* — Eisa B Elhilo
(74) *Attorney, Agent, or Firm* — Polsinelli PC

(57) ABSTRACT

The instant disclosure relates to hair coloring base compositions and developer compositions that can be incorporated into a hair color cartridge, which combines the compositions and dispenses them onto hair. The hair color cartridge includes: (a) one or more hair coloring base compositions and; (b) one or more developer compositions, which can be combined to form an active hair coloring composition and dispensed onto hair. The hair coloring base compositions typically include one or more oxidative dye precursors; one or more alkalizing agents; one or more reducing agents; optionally, one or more cationic conditioning polymers; one or more surfactants; one or more water-soluble solvents; and water. The developer compositions typically include one or more oxidizing agents; one or more surfactants; and water. The unique components and fluid characteristics of the various compositions are such that devices or appliances comprising them accurately combine and dispense the hair coloring base composition(s) with the developer composition(s) in a predetermined ratio with excellent consistency for application to hair.

20 Claims, 1 Drawing Sheet

(51) Int. Cl.
*A61K 8/41* (2006.01)
*A61K 8/46* (2006.01)
*A61K 8/81* (2006.01)
*A61K 8/34* (2006.01)
*A61K 8/36* (2006.01)
*A61K 8/42* (2006.01)
*A61K 8/33* (2006.01)
*A61K 8/86* (2006.01)
*A45D 34/04* (2006.01)
*A46B 11/00* (2006.01)
*A46B 13/04* (2006.01)
*A46B 15/00* (2006.01)
*A46B 9/02* (2006.01)
*A61K 8/19* (2006.01)
*A45D 34/00* (2006.01)
*A45D 19/00* (2006.01)

(52) U.S. Cl.
CPC ...... *A46B 11/0041* (2013.01); *A46B 11/0062* (2013.01); *A46B 11/0065* (2013.01); *A46B 11/0072* (2013.01); *A46B 13/04* (2013.01); *A46B 15/0059* (2013.01); *A61K 8/19* (2013.01); *A61K 8/33* (2013.01); *A61K 8/34* (2013.01); *A61K 8/342* (2013.01); *A61K 8/345* (2013.01); *A61K 8/361* (2013.01); *A61K 8/411* (2013.01); *A61K 8/42* (2013.01); *A61K 8/46* (2013.01); *A61K 8/817* (2013.01); *A61K 8/86* (2013.01); *A61Q 5/10* (2013.01); *A45D 19/0066* (2021.01); *A45D 2034/005* (2013.01); *A45D 2200/058* (2013.01); *A46B 2200/104* (2013.01); *A61K 2800/4324* (2013.01); *A61K 2800/87* (2013.01); *A61K 2800/88* (2013.01); *A61K 2800/882* (2013.01)

(58) Field of Classification Search
CPC ............ A61K 8/342; A61K 2800/4324; A61K 2800/88; A61K 2800/882; A61K 8/347; A61K 8/416; A61K 8/34; A61K 8/345; A61K 8/46; A61K 2800/5426; A61K 8/375; A61K 8/676; A61K 2800/522
USPC ........................................................... 8/405
See application file for complete search history.

(56) References Cited

U.S. PATENT DOCUMENTS

| | | | |
|---|---|---|---|
| 8,632,611 B2* | 1/2014 | Agostino | A61K 8/731 8/405 |
| 9,283,158 B2* | 3/2016 | Goutsis | A61K 8/73 |
| 2010/0322876 A1 | 12/2010 | Nguyen et al. | |
| 2013/0220358 A1* | 8/2013 | Agostino | A61K 8/737 132/208 |
| 2014/0237736 A1* | 8/2014 | Allard | A61K 8/90 8/416 |
| 2016/0143408 A1 | 5/2016 | Grez | |
| 2016/0151264 A1 | 6/2016 | Charrier et al. | |
| 2016/0166032 A1 | 6/2016 | Grez | |
| 2016/0183664 A1 | 6/2016 | Grez | |
| 2016/0158582 A1 | 7/2016 | Mueller et al. | |

* cited by examiner

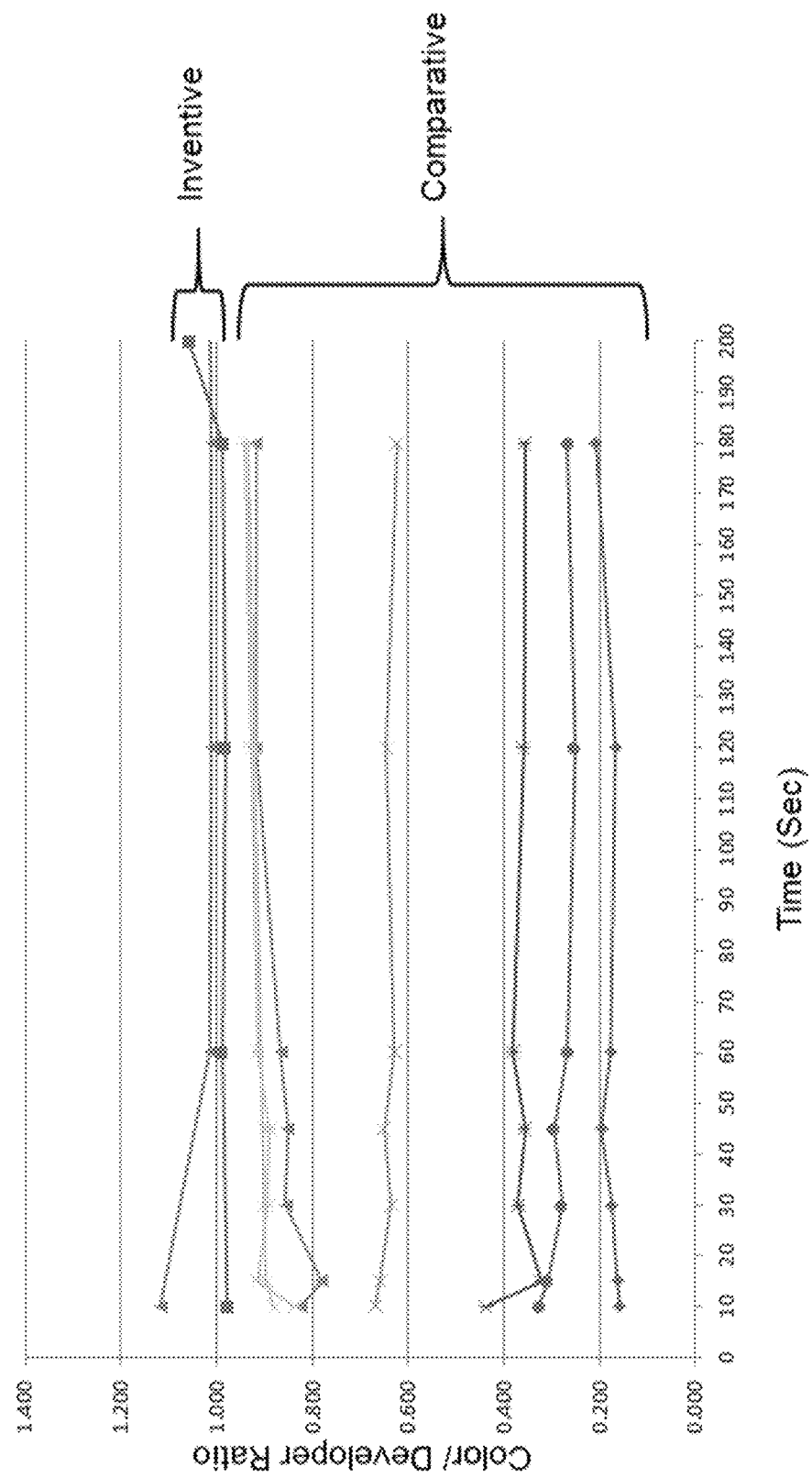

HAIR COLOR CARTRIDGE AND COMPOSITIONS FOR USE IN THE HAIR COLOR CARTRIDGE

CROSS-REFERENCE TO RELATED APPLICATIONS

This application claims priority to and is a continuation of U.S. patent application Ser. No. 15/850,828, filed on Dec. 21, 2017, the entirety of which is herein incorporated by reference.

FIELD OF THE DISCLOSURE

The present disclosure relates to a hair color cartridge containing one or more hair coloring base compositions and one or more developer compositions. These compositions are combined to form an active hair coloring composition that is dispensed onto hair, for example, when the cartridge is used in a hair coloring device or appliance.

BACKGROUND

Individuals often seek to change the color of their hair. Hair dyeing products for permanently altering the color of hair typically rely on a combination of compositions. For example, compositions containing oxidative dye precursors (also known as primary intermediates or oxidation bases) and compositions containing oxidizing agents such as peroxide and persulfate compounds.

Oxidative dye precursors are often colorless or weakly colored compounds, which, when combined with oxidizing agents, transition to provide colored species via a process of oxidative condensation. The shades obtained with oxidative dye precursors may be varied by combining them with one or more couplers. Couplers include, for example, aromatic meta-diamines, meta-aminophenols, meta-diphenols, and certain heterocyclic compounds, such as indole compounds.

The oxidizing agent(s) employed in permanent dyeing compositions may degrade the melanin of the hair, which, depending on the nature of the oxidizing agent, may lead to less pronounced lightening of the fibers. Thus, for relatively weak lightening, the at least one oxidizing agent may be, for example, hydrogen peroxide. When more substantial lightening is desired, peroxygenated salts, such as persulfates, may be used, usually in the presence of hydrogen peroxide.

Hair dyeing compositions typically contain an alkalizing agent such as aqueous ammonia. The alkalizing agents activate the oxidizing agent and also cause the hair shaft to swell, thus allowing the small oxidative dye precursor molecules to penetrate the cuticle and cortex before the oxidation condensation process is completed. The resulting larger-sized colored complexes from the oxidative reaction are then trapped inside the hair fiber, thereby permanently altering the color of the hair.

The duration for which dyed hair remains colored should be limited only by hair growth rate. As new hair grows from the roots of the hair, the natural color of the hair begins to appear. Unfortunately, the color (and the quality of the color) of the artificially colored hair tends to degrade over time. For example, repeated shampooing, combing and brushing, and exposure to sunlight, oxygen, and heat, can cause the color to fade. Red colors, for instance, are particularly susceptible to these degrading processes.

Mixing and applying hair dye can be messy. The hair dye may drip or easily run from the hairline to the face, neck, or other areas of the body for which the hair dye is not intended. The strong chemicals typically included in hair dye can therefore burn, stain, or irritate these areas. Devices for applying hair dye often are inconsistent in the mixing and dispensing of the hair dye, and can cause unwanted hair dye to come into contact with a user's hands, etc. If a specialized mixing and dispensing device is not used, one must manually combine a hair coloring base composition with a developer composition in a bowl or similar container, and mix the two components with a mixing utensil. The mixture is then applied to the hair using protective gloves. This scenario results in the mixing bowl(s), the mixing utensil(s), and the mixing gloves being contaminated with the hair dye, which should be on the hair.

SUMMARY OF THE DISCLOSURE

The present disclosure relates to hair coloring base compositions and developer compositions that are included in hair color cartridges, which may be used in conjunction with hair coloring devices or appliances for coloring hair. The hair coloring base compositions and the developer compositions are combined to provide an active hair coloring composition. The hair coloring base compositions, the developer compositions, and the active hair coloring compositions, are unique in their compatibility with devices or appliance in which the cartridges are used. For example, the unique components and fluid characteristics of the hair coloring base compositions and the developer compositions are such that they can be accurately combined in predetermined ratios with excellent consistency. Furthermore, the active hair coloring compositions have physical and chemical properties (consistency, viscosity, stickiness, etc.) that result in less dripping and unwanted running of the active hair coloring compositions to the face, neck, or other areas where the active hair coloring composition is not intended to be applied. The active hair coloring compositions easily flow around the hair fibers to provide improved (uniform) coverage without being messy.

The hair coloring base compositions typically include:
one or more oxidative dye precursors;
one or more alkalizing agents;
one or more reducing agents;
optionally, one or more cationic conditioning polymers;
one or more surfactants;
one or more water-soluble solvents; and
water.
The developer compositions typically include:
one or more oxidizing agents;
one or more surfactants; and
water.

One or more hair coloring base compositions and one or more developer compositions may be separately housed or packaged, for example, in individual chambers or packets of a hair color cartridge. When a consumer or stylist is ready to color hair, one or more of the coloring base compositions is combined with one or more developer compositions to form an active hair coloring composition that may be dispensed onto hair, for example, using a dispensing device or appliance. The hair coloring base composition(s) and the developer composition(s) are typically combined in a particular ratio, which may be predetermined, for example, a ratio of about 5:1 to about 1:5, a ratio of about 1:3 to about 3:1, or a ratio of about 1:2 to about 2:1.

Non-limiting examples of oxidative dye precursors include ortho- and/or para-aminophenols, ortho- and/or para-phenylenediamines, double bases, heterocyclic bases, acid addition salts thereof, and a mixture thereof. In addition to oxidative dye precursors, the hair coloring base composition may also include one or more couplers. Non-limiting examples of couplers include aromatic meta-diamines, meta-aminophenols, meta-diphenols, and certain heterocyclic compounds, such as indole compounds.

Non-limiting examples of alkalizing agents that may be included in the hair coloring base compositions include ammonia, ammonium hydroxide, ammonium carbonate, ammonium chloride, ammonium sulfate, ammonium nitrate, ammonium phosphate, ammonium acetate, ammonium hydrogen carbonate, ammonium carbamate, percarbonate salts, alkanolamines (such as monoethanolamine, diethanolamine, triethanolamine, monopropanolamine, dipropanolamine, tripropanolamine, 2-amino-2-methyl-1,3-propanediol, 2-amino-2-methyl-1-propanol, and 2-amino-2-hydroxymethyl-1,3-propanediol), guanidium salts, alkali metal hydroxides (such as sodium hydroxide), alkali metal carbonates, sodium silicate, sodium metasilicate and a mixture thereof.

Non-limiting examples of reducing agents include ammonium bisulfite, ammonium sulfite, potassium metabisulfite, potassium sulfite, sodium hydrosulfite, sodium metabisulfite, sodium sulfite, sodium bisulphite, thioglycolic acid, thiolactic acid, dehydroascorbic acid, a salt thereof, and a mixture thereof.

Polyquaterniums are one group of cationic conditioning polymers that may be used but are certainly not the only cationic conditioning polymers useful herein.

The hair coloring base composition may include one or more anionic surfactants, one or more nonionic surfactants, one or more amphoteric surfactants (zwitterionic surfactants), or a mixture thereof. Nonetheless, in some instances, the hair coloring base composition includes at least one or more anionic surfactants, one or more nonionic surfactants, or a mixture thereof; and in particular includes both one or more anionic surfactants and one or more nonionic surfactants.

Non-limiting examples of water-soluble solvents include glycerin, alcohols, organic solvents, polyols, glycols, and a mixture thereof.

With respect to the developer composition, non-limiting examples of oxidizing agents include hydrogen peroxide, inorganic alkali metal peroxides (such as sodium periodate and sodium peroxide), organic peroxides (such as urea peroxide and melamine peroxide), inorganic perhydrate salts (such as the alkali metal salts of perborates, percarbonates, perphosphates, persilicates, persulphates), bromates, and a mixture thereof.

The developer composition may include one or more anionic surfactants, one or more nonionic surfactants, one or more amphoteric surfactants (zwitterionic surfactants), or a mixture thereof. Nonetheless, in some instances, the developer composition includes at least one or more nonionic surfactants.

The hair coloring base compositions and the developer compositions may be incorporated into a hair color cartridge having individual packets or chambers that separately house each of the one or more hair coloring base compositions and each of the one or more developer compositions. Each individual packet or chamber may include an individual pump for delivering the content of the packet or chamber to a mixing assembly. Alternatively, only one (or more than one) pump may be integrated with multiple packets or chambers. A control assembly operable in response to a user's input can control each of the one or more pumps to deliver selected amounts of the one or more hair coloring base compositions and the one or more developer compositions to a mixing assembly which mixes the compositions to form an active hair coloring composition. The mixing assembly may then deliver the active hair coloring composition to a receptacle (holding receptacle) or directly to a brushhead/distributor, for example, a brushhead/distributor that is mountable in a handle having a motor which activates the brushhead/distributor, for example, by driving the brushhead/distributor in a linear oscillating manner.

The hair color cartridges may be incorporated into or combined with a hair coloring device or appliance. For example, the cartridge may be incorporated into or be part of a single-use or multi-use hair coloring device or appliance. The device or appliance may have a portal member or connecting means capable of receiving the cartridge; a mixing assembly to combine the hair coloring base composition(s) and the developer composition(s) to form an active hair coloring composition; optionally a holding receptacle for the active hair coloring composition; and a brushhead/dispenser member that is in fluid communication with the active hair coloring composition; wherein active hair coloring composition is directed to the brushhead/dispenser by a user or by a pump operating on the device or appliance.

The instant disclosure is also related to methods for coloring hair. The methods typically include dispensing an active hair coloring composition to the hair, for example, from a device or appliance, as disclosed herein. The active hair coloring composition is applied to the hair and allowed to remain on the hair for a period of time, for example, a period of time sufficient for imparting a color change to the hair. For example, the active hair coloring composition may be allowed to remain on the hair for about 5 minutes to about 2 hours. After the active hair coloring composition is allowed to remain on the hair for a period of time, it is typically rinsed from the hair with water. Upon rinsing, the hair may also be shampooed and/or conditioned with a shampoo and/or conditioner.

BRIEF DESCRIPTION OF THE DRAWINGS

Implementations of the present technology will now be described, by way of example only, with reference to the attached figures, wherein:

FIG. 1 is a graph comparing the mix ratios of a hair coloring base composition and a developer composition dispensed from a hair coloring device according to the instant disclosure with the mix ratios of comparative commercial compositions dispensed from the same hair coloring device.

It should be understood that the various aspects are not limited to the arrangements and instrumentality shown in the drawings.

DETAILED DESCRIPTION OF THE DISCLOSURE

The present disclosure relates to hair coloring base compositions, developer compositions, hair color cartridges comprising the compositions, and devices or appliances for use with the hair color cartridges. A hair coloring base composition and a developer composition are combined to form an active hair coloring composition for application to hair. In particular, one or more hair coloring base compositions and one or more developer compositions can be incorporated into a cartridge having several individual packets or chambers, wherein each of the individual compositions are separately contained or housed in the individual packets or chambers. The hair color cartridge may be incorporated into or be part of a device or appliance, or the hair color cartridge can be attached to a device or appliance, for coloring hair. With respect to the compositions, the hair coloring base compositions typically include:

one or more oxidative dye precursors;
one or more alkalizing agents;
one or more reducing agents;
optionally, one or more cationic conditioning polymers;
one or more surfactants;
one or more water-soluble solvents; and
water; and The developer compositions typically include:
one or more oxidizing agents;
one or more surfactants; and
water.

The hair coloring base composition and the developer composition may be combined in a particular ratio, which may be predetermined, for example, a ratio of about 5:1 to about 1:5, 1:4 to 4:1, a ratio of about 1:3 to about 3:1, a ratio of about 1:2 to about 2:1, or a ratio of about 1:1.

Hair coloring base compositions typically include one or more oxidative dye precursors, which may also be referred to as "primary intermediates" or "oxidation bases." Oxidative dye precursors are often colorless or weakly colored compounds, which, when combined with oxidizing products, reactive via oxidative condensation to provide colored species. Non-limiting examples of oxidative dye precursors include aromatic diamines, polyhydric phenols, amino phenols, and derivatives of these compounds, such as, for example, N-substituted derivatives of the amines, and ethers of the phenols, ortho- or para-aminophenols, ortho- or para-phenylenediamines, double bases, heterocyclic bases, and the acid addition salts thereof. A more exhaustive but non-limiting list of oxidative dye precursors that may be included in the hair coloring base compositions is provided later, under the heading "Oxidative Dye Precursors."

The shades obtained with oxidative dye precursors may often be varied by combining them with at least one coupler. Thus, the hair coloring base compositions of the instant disclosure may include one or more couplers. Non-limiting examples of couplers include aromatic meta-diamines, meta-aminophenols, meta-diphenols, and certain heterocyclic compounds, such as indole compounds. A more exhaustive but non-limiting list of couplers that may be included in the hair coloring base compositions is provided later, under the heading "Couplers." The variety of molecules used as oxidative dye precursors and couplers allow for a wide range of colors to be obtained. Moreover, the hair coloring base composition may additionally include one or more direct dyes, pigments, and mixtures thereof.

The total amount of the one or more oxidative dye precursors may vary but in some cases is often about 0.0001 to about 15 wt. %, based on the total weight of the hair coloring base composition. In some instances, the total amount of the one or oxidative dye precursors is about 0.0001 to about 12 wt. %, about 0.0001 to about 10 wt. %, about 0.0001 to about 8 wt. %, about 0.0001 to about 5 wt. %, about 0.001 to about 12 wt. %, about 0.001 to about 10 wt. %, about 0.001 to about 8 wt. %, about 0.001 to about 5 wt. %, about 0.005 to about 10 wt. %, about 0.005 to about 8 wt. %, about 0.005 to about 6 wt. %, or about 0.005 to about 5 wt. %, based on the total weight of the hair coloring base composition.

As noted above, couplers may also be included in the hair coloring base composition. The total amount of couplers may also vary, but in general, the total amount of one or more couplers may be about 0.0001 to about 15 wt. %, based on the total weight of the hair coloring base composition. In some instances, the total amount of the one or couplers is about 0.0001 to about 12 wt. %, about 0.0001 to about 10 wt. %, about 0.0001 to about 8 wt. %, about 0.0001 to about 5 wt. %, about 0.001 to about 12 wt. %, about 0.001 to about 10 wt. %, about 0.001 to about 8 wt. %, about 0.001 to about 5 wt. %, about 0.005 to about 10 wt. %, about 0.005 to about 8 wt. %, about 0.005 to about 6 wt. %, or about 0.005 to about 5 wt. %, based on the total weight of the hair coloring base composition.

The one or more alkalizing agents that may be included in the hair coloring base can have multiple roles in the coloring process. For instance, the alkalizing agent typically causes the hair shaft to swell, thus allowing the small oxidative dye precursor molecules to more easily penetrate the cuticle and cortex. Also, the alkalize agent can activate the oxidizing agent(s) of the developer composition and contribute to the oxidation condensation process. Non-limiting examples of alkalizing agents include ammonia, ammonium hydroxide, ammonium carbonate, ammonium chloride, ammonium sulfate, ammonium nitrate, ammonium phosphate, ammonium acetate, ammonium hydrogen carbonate, ammonium carbamate, percarbonate salts, alkanolamines (such as monoethanolamine, diethanolamine, triethanolamine, monopropanolamine, dipropanolamine, tripropanolamine, 2-amino-2-methyl-1,3-propanediol, 2-amino-2-methyl-1-propanol, and 2-amino-2-hydroxymethyl-1,3-propanediol), guanidium salts, alkali metal hydroxides (such as sodium hydroxide), alkali metal carbonates, and a mixture thereof. In some cases, alkalizing agents such as ammonia and/or alkanolamines are particularly useful, for example, ammonia, ammonium hydroxide, and/or monoethanolamine.

The total amount of alkalizing agent(s) in the hair coloring base composition can vary but in some cases may be about 0.1 to about 40 wt. %, based on the total weight of the hair coloring base composition. In some cases, the total amount of the one or more alkalizing agents is about 0.1 to about 30 wt. %, about 0.1 to about 25 wt. %, about 0.1 to about 20 wt. %, about 0.1 to about 15 wt. %, about 0.1 to about 10 wt. %, about 0.5 to about 10 wt. %, about 1 to about 40 wt. %, about 1 to about 30 wt. %, about 1 to about 25 wt. %, about 1 to about 20 wt. %, about 1 to about 15 wt. %, or about 1 to about 10 wt. %, based on the total weight of the hair coloring base composition.

The one or more neutralizing agents that may be included in the hair coloring base compositions can vary, but in some case may be selected from the group consisting of ammonium bisulfite, ammonium sulfite, potassium metabisulfite, potassium sulfite, sodium hydrosulfite, sodium metabisulfite, sodium sulfite, sodium bisulphite, thioglycolic acid, thiolactic acid, dehydroascorbic acid, a salt thereof, and a mixture thereof. The salts referred to throughout the disclosure may include salts having a counter-ion such as an alkali metal, alkaline earth metal, or ammonium counterion. This list of counterions, however, is non-limiting. In some instances, a particularly useful reducing agent is a thiolactate, for example, ammonium thiolactate.

Furthermore, the one or more reducing agents may be selected from the group consisting of thiols such as thioglycolic acid or a salt thereof, thiolactic acid or a salt thereof, 3-mercaptopropionic acid, thiomalic acid, 2,3-dimercaptosuccinic acid, cysteine, N-glycyl-L-cysteine, L-cysteinylglycine and also esters and salts thereof, thioglycerol, cysteamine and $C_1$-$C_4$ acyl derivatives thereof, N-mesylcysteamine, N-acetylcysteine, N-mercaptoalkylamides of sugars such as N-(mercapto-2-ethyl) gluconamide, pantetheine, N-(mercaptoalkyl)-$\Omega$-hydroxyalkylamides, N-monoor N,N-dialkylmercapto-4-butyramides, aminomercaptoalkylamides, N-(mercaptoalkyl)succinamic acids and N-(mercaptoalkyl)succinimides, alkylamino mercaptoalkyl amides, mercaptoalkylaminoamides, N-mercaptoalkylalkanediamides, ammonium bisulfite, ammonium sulfite, potassium metabisulfite, potassium sulfite, sodium hydrosulfite, sodium metabisulfite, sodium sulfite, sodium bisulphite, and a mixture thereof.

In some cases, the one or more reducing agents are selected from the group consisting of ammonium bisulfite, ammonium sulfite, potassium metabisulfite, potassium sulfite, sodium hydrosulfite, sodium metabisulfite, sodium sulfite, sodium bisulphite, thioglycolic acid, thiolactic acid, dehydroascorbic acid, a salt thereof, and a mixture thereof.

The reducing agent may be chosen from hydrides such as sodium or potassium borohydride or alkali metal or alkaline-earth metal sulfites or bisulfites; or alternatively from phosphorus derivatives such as phosphines or phosphites.

The total amount of the one more reducing agents in the hair coloring base composition may vary but is typically about 0.01 to about 20 wt. %, based on the total weight of the composition. The total amount of the one or more reducing agents may be about 0.01 to about 15 wt. %, about 0.01 to about 10 wt. %, about 0.1 to about 20 wt. %, about 0.1 to about 15 wt. %, or about 0.1 to about 10 wt. %, based on the total weight of the hair coloring base composition.

The hair coloring base compositions may include one or more cationic conditioning polymers. Examples of cationic conditioning polymers that can be used include, without limitation, cationic cellulose, cationic proteins, and cationic polymers. The cationic polymers can have a vinyl group backbone of amino and/or quaternary ammonium monomers. Cationic amino and quaternary ammonium monomers include, without limitation, dialkylamino alkylmethacrylate, monoalkylaminoalkyl acrylate, monoalkylaminoalkyl methacrylate, trialkyl methacryoloxyalkyl ammonium salt, trialkyl acryloxyalkyl ammonium salts, diallyl quaternary ammonium salts, vinyl compounds substituted with dialkyl aminoalkyl acrylate, and vinyl quaternary ammonium monomers having cyclic cationic nitrogen containing rings such as pyridinium, imidazolium, or quaternized pyrrolidine.

Other examples of cationic conditioning polymers that can be used include, without limitation, hydroxypropyltrimonium honey, cocodimonium silk amino acids, cocodimonium hydroxypropyl hydrolyzed wheat or silk protein, polyquaternium-5, polyquaternium-11, polyquaternium-2, polyquaternium-4, polyquaternium-6, polyquaternium-7, polyquaternium-14, polyquaternium-16, polyquaternium-22, polyquaternium-10, and guar hydroxypropyltrimonium chloride. In some instances one or more polyquaterniums are particularly useful, for example, those listed above, and in particular, polyquaternium-6. A more exhaustive but non-limiting list of cationic conditioning polymer that may be included in the hair coloring base compositions is provided later, under the heading "Cationic Conditioning Polymers."

The total amount of the one or more cationic conditioning polymers can vary but is typically about 0.1 to about 15 wt. %, based on the total weight of the hair coloring base composition. Furthermore, the total amount of the one or more cationic conditioning polymers may be about 0.1 to about 10 wt. %, about 0.1 to about 8 wt. %, about 0.1 to about 5 wt. %, about 0.5 to about 15 wt. %, about 0.5 to about 10 wt. %, about 0.5 to about 8 wt. %, about 0.5 to about 5 wt. %, about 1 to about 15 wt. %, about 1 to about 10 wt. %, about 1 to about 8 wt. %, or about 1 to about 5 wt. %, based on the total weight of the hair coloring base composition.

The hair coloring base composition may include one or more anionic surfactants, one or more nonionic surfactants, one or more amphoteric surfactants (zwitterionic surfactants), or a mixture thereof.

The total amount of the one or more surfactants can vary but is typically about 1 to about 35 wt. %, based on the total weight of the hair coloring base composition. The total amount of the one or more surfactants may be about 1 to about 30 wt. %, about 1 to about 25 wt. %, about 5 to about 35 wt. %, about 5 to about 30 wt. %, about 5 to about 25 wt. %, about 10 to about 35 wt. %, about 10 to about 30 wt. %, or about 10 to about 25 wt. %, based on the total weight of the hair coloring base composition.

In some instances, the hair coloring base composition includes at least one or more anionic surfactants, one or more nonionic surfactants, or a mixture thereof; and in particular includes both one or more anionic surfactants and one or more nonionic surfactants. In some instances, the hair coloring base compositions may be free or essentially free of amphoteric surfactants; and in some cases the hair coloring base compositions may be free or essentially free of cationic surfactants.

With respect to nonionic surfactants, in some instances, the hair coloring base composition include one or more nonionic surfactants selected from the group consisting of oxyethylenatedamides, fatty alcohols, oxyethylenated fatty alcohols, and block-copolymer (polycondensate) surfactants of ethylene oxide and of propylene oxide, and a mixture thereof. For example, the hair coloring base composition may include oleyl alcohol (fatty alcohol), PEG-4 rapeseedamide (an oxyethylenated amide), deceth-3 (an oxyethylenated fatty alcohol), poloxamer 338 (block-copolymer (polycondensate) surfactants of ethylene oxide and of propylene oxide), or a combination thereof.

Non-limiting examples of nonionic oxyethylenated amides are those of the following formula:

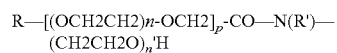

in which:

p denotes 0 or 1, n denotes a number ranging from 1 to 10 and preferably from 1 to 6, n' denotes a number ranging from 1 to 100 and preferably from 1 to 60, R' denotes a hydrogen atom or a CH2CH2OH radical and preferably a hydrogen atom, and R denotes a C10-C30 and preferably C12-C22 alkyl or alkenyl radical.

Examples of these compounds include AMIDET A15 sold by the company Kao (INCI name: Trideceth-2 carboxamide MEA), ETHOMID HP 60 sold by the company Akzo Nobel (INCI name: PEG-50 Hydrogenated Palmamide) and AMIDET N sold by the company Kao (INCI name: PEG-4 Rapeseedamide).

In some cases, the hair coloring base compositions includes at least rapeseed amide oxyethylenated with 4 oxyethylene units (PEG-4 rapeseedamide).

Non-limiting examples of fatty alcohols include saturated or unsaturated and linear or branched alcohols comprising from 6 to 30 carbon atoms and preferably from 8 to 30 carbon atoms, for instance, cetyl alcohol, isostearyl alcohol, stearyl alcohol and the mixture thereof (cetylstearyl alcohol), octyldodecanol, 2-butyloctanol, 2-hexyldecanol, 2-undecylpentadecanol, oleyl alcohol, linolenyl alcohol, ricinoleyl alcohol, undecylenyl alcohol and linoleyl alcohol, and mixtures thereof.

Non-limiting examples of oxyethylenated fatty alcohols include those comprising less than 10 OE units, preferably chosen from oxyethylenated derivatives of saturated or unsaturated, linear or branched, preferably linear, $C_8$-$C_{30}$ and preferably $C_{12}$-$C_{22}$ fatty alcohols, for instance cetyl alcohol, oleyl alcohol, oleocetyl alcohol, lauryl alcohol, behenyl alcohol, cetearyl alcohol, stearyl alcohol and isostearyl alcohol, and mixtures thereof.

As oxyethylenated fatty alcohols comprising less than 10 OE units, mention may be made of oxyethylenated fatty alcohols comprising from 2 to 8 and preferably from 2 to 6 OE units, for instance products of addition of ethylene oxide and lauryl alcohol, for instance lauryl alcohol 2 OE (CTFA name: laureth-2), products of addition of ethylene oxide and stearyl alcohol, for instance stearyl alcohol 2 OE (CTFA name: steareth-2), products of addition of ethylene oxide and decyl alcohol, for instance decyl alcohol 3 OE (CTFA name: deceth-3), decyl alcohol 5 OE (CTFA name: deceth-5), products of addition of ethylene oxide and oleocetyl alcohol, for instance oleocetyl alcohol 5 OE (CTFA name: oleoceteth-5), and mixtures thereof. In some instances, deceth-3 may be particularly useful.

Furthermore, non-limiting examples of oxyethylenated fatty alcohols having an average degree of ethoxylation of 2 to 29 are, for example, laureth-2, oleth-2, ceteareth-2, laneth-2, laureth-3, oleth-3, ceteareth-3, laureth-4, oleth-4, ceteareth-4, laneth-4, laureth-5, oleth-5, ceteareth-5, laneth-5, deceth-4, deceth-7, laureth-7, oleth-7, coceth-7, ceteth-7, ceteareth-7, C11-15 pareth-7, laureth-9, oleth-9, ceteareth-9, laureth-10, oleth-10, beheneth-10, ceteareth-10, laureth-12, ceteareth-12, trideceth-12, ceteth-15, laneth-15, ceteareth-15, laneth-16, ceteth-16, oleth-16, steareth-16, oleth-20, ceteth-20, ceteareth-20, laneth-20, steareth-21, ceteareth-23, ceteareth-25, ceteareth-27, and a mixture thereof.

In some cases, the hair coloring base composition includes both at least one nonionic surfactant chosen from oxyethylenated amide and at least one nonionic surfactant chosen from oxyethylenated (OE) fatty alcohol comprising less than 10 OE units, that may be chosen among those described above.

Furthermore, the hair coloring base composition may include one or more nonionic surfactants that is a block-copolymer (polycondensate) surfactant of ethylene oxide and of propylene oxide. The block-copolymer (polycondensate) surfactant of ethylene oxide and of propylene oxide may have a weight-average molecular weight ranging from 1000 to 20000, better from 1500 to 19000, from 2000 to 18000, or from 4000 to 17000.

Mention may be made, as block-copolymer (polycondensate) surfactant of ethylene oxide and of propylene oxide which may be used, of the polyethylene glycol/polypropylene glycol/polyethylene glycol triblock polycondensates sold under the "SYNPERONIC" names, such as "SYNPERONIC PE/F32" (INCI name: Poloxamer 108), "SYNPERONI. PE/F108" (INCI name: Poloxamer 338), "SYNPERONIC PE/L44" (INCI name: Poloxamer 124), "SYNPERONIC PE/L42" (INCI name: Poloxamer 122), "SYNPERONIC PE/F127" (INCI name: Poloxamer 407), "SYNPERONIC PE/F88" (INCI name: Poloxamer 238) or "SYNPERONIC PE/L64" (INCI name: Poloxamer 184), by Croda or also "LUTROL F68" (INCI name: Poloxamer 188), sold by BASF. In some instances, Poloxamer 338 may be particularly useful.

A more exhaustive list of useful nonionic surfactants that may be included in the hair coloring base composition is provided later, under the heading "Nonionic Surfactants."

The total amount of the one or more nonionic surfactants that may be included in the hair coloring base composition may vary but is typically about 1 to about 30 wt. %, based on the total weight of the hair coloring base composition. The total amount of the one or more surfactants may be about 1 to about 25 wt. %, about 1 to about 20 wt. %, about 5 to about 25 wt. %, about 5 to about 30 wt. %, about 5 to about 25 wt. %, about 5 to about 20 wt. %, about 10 to about 30 wt. %, about 10 to about 25 wt. %, or about 10 to about 20 wt. %, based on the total weight of the hair coloring base composition.

Many anionic surfactants are known and may be optionally included in the hair coloring base composition. For example, anionic surfactants include alkyl carboxylic acids, alkyl ether carboxylic acids, alkyl phosphates, alkyl ether phosphates, alkyl sulfates, alkyl ether sulfates, alkyl sulfonates, alkyl ether sulfonates, and salts thereof.

In some cases, the anionic surfactant is one or more alkyl ether carboxylic acid. Suitable non-limiting examples of alkyl ether carboxylic acids include ceteareth-2 carboxylic acid, ceteareth-10 carboxylic acid, coceth-7 carboxylic acid, laureth-4 carboxylic acid, laureth-5 carboxylic acid, laureth-6 carboxylic acid, myreth-2 carboxylic acid, myreth-3 carboxylic acid, myreth-4 carboxylic acid, myreth-5 carboxylic acid, myreth-6 carboxylic acid, steareth-2 carboxylic acid, steareth-4 carboxylic acid, steareth-5 carboxylic acid, steareth-6 carboxylic acid, oleth-2 carboxylic acid, oleth-4 carboxylic acid, and mixtures and/or salts thereof.

The total amount of the one or more anionic surfactants, if present, may vary but is typically about 0.1 to about 15 wt. %, based on the total weight of the hair coloring base composition. The total amount of the one or more anionic surfactants can be about 0.1 to about 12 wt. %, about 0.1 to about 10 wt. %, about 0.1 to about 8 wt. %, about 0.1 to about 6 wt. %, about 0.5 to about 15 wt. %, about 0.5 to about 12 wt. %, about 0.5 to about 10 wt. %, about 0.5 to about 8 wt. %, about 0.5 to about 6 wt. %, about 1 to about 15 wt. %, about 1 to about 12 wt. %, about 1 to about 10 wt. %, about 1 to about 8 wt. %, or about 1 to about 6 wt. %, based on the total weight of the hair coloring base composition.

Water-soluble solvents may be included in the hair coloring base composition. The term "water-soluble solvent" is interchangeable with the term "water-miscible solvent" and means a compound that is liquid at 25° C. and at atmospheric pressure (760 mmHg), and it has a solubility of at least 50% in water under these conditions. In some cases, the water soluble solvents has a solubility of at least 60%, 70%, 80%, or 90%. Non-limiting examples of water-soluble solvents include, for example, glycerin, alcohols (for example, C1-30, C1-15, C1-10, or C1-4 alcohols), organic solvents, polyols, glycols, and a mixture thereof.

As examples of organic solvents, non-limiting mentions can be made of monoalcohols and polyols such as ethyl alcohol, isopropyl alcohol, propyl alcohol, benzyl alcohol, and phenylethyl alcohol, or glycols or glycol ethers such as, for example, monomethyl, monoethyl and monobutyl ethers of ethylene glycol, propylene glycol or ethers thereof such as, for example, monomethyl ether of propylene glycol, butylene glycol, hexylene glycol, dipropylene glycol as well as alkyl ethers of diethylene glycol, for example monoethyl ether or monobutyl ether of diethylene glycol. Other suitable examples of organic solvents are ethylene glycol, propylene glycol, butylene glycol, hexylene glycol, propane diol, and glycerin. The organic solvents can be volatile or non-volatile compounds.

Further non-limiting examples of water-soluble solvents include alkanediols (polyhydric alcohols) such as glycerin, 1,2,6-hexanetriol, trimethylolpropane, ethylene glycol, propylene glycol, diethylene glycol, triethylene glycol, tetraethylene glycol, pentaethylene glycol, dipropylene glycol, 2-butene-1,4-diol, 2-ethyl-1,3-hexanediol, 2-methyl-2,4-pentanediol, (caprylyl glycol), 1,2-hexanediol, 1,2-pentanediol, and 4-methyl-1,2-pentanediol; alkyl alcohols having 1 to 4 carbon atoms such as ethanol, methanol, butanol, propanol, and isopropanol; glycol ethers such as ethylene glycol monomethyl ether, ethylene glycol monoethyl ether, ethylene glycol monobutyl ether, ethylene glycol monomethyl ether acetate, diethylene glycol monomethyl ether, diethylene glycol monoethyl ether, diethylene glycol mono-n-propyl ether, ethylene glycol mono-iso-propyl ether, diethylene glycol mono-iso-propyl ether, ethylene glycol mono-n-butyl ether, ethylene glycol mono-t-butyl ether, diethylene glycol mono-t-butyl ether, 1-methyl-1-methoxybutanol, propylene glycol monomethyl ether, propylene glycol monoethyl ether, propylene glycol mono-t-butyl ether, propylene glycol mono-n-propyl ether, propylene glycol mono-iso-propyl ether, dipropylene glycol monomethyl ether, dipropylene glycol monoethyl ether, dipropylene glycol mono-n-propyl ether, and dipropylene glycol mono-iso-propyl ether; 2-pyrrolidone, N-methyl-2-pyrrolidone, 1,3-dimethyl-2-imidazolidinone, formamide, acetamide, dimethyl sulfoxide, sorbit, sorbitan, acetine, diacetine, triacetine, sulfolane, and a mixture thereof.

In some cases, the water-soluble solvent may be selected from the group consisting of one or more glycols, $C_{1-4}$ alcohols, glycerin, and a mixture thereof. In some cases, the water-soluble solvent is selected from the group consisting of caprylyl glycol, glycerin, ethanol, isopropyl alcohol, and a mixture thereof. Dipropylene glycol, propylene glycol, hexylene glycol, caprylyl glycol, propylene glycol, glycerin, ethanol, and a mixture thereof.

Polyhydric alcohols are useful. Examples of polyhydric alcohols include glycerin, ethylene glycol, diethylene glycol, triethylene glycol, propylene glycol, dipropylene glycol, tripropylene glycol, 1,3-butanediol, 2,3-butanediol, 1,4-butanediol, 3-methyl-1,3-butanediol, 1,5-pentanediol, tetraethylene glycol, 1,6-hexanediol, 2-methyl-2,4-pentanediol, polyethylene glycol, 1,2,4-butanetriol, 1,2,6-hexanetriol, and a mixture thereof. Polyol compounds may also be used. Non-limiting examples include the aliphatic diols, such as 2-ethyl-2-methyl-1,3-propanediol, 3,3-dimethyl-1,2-butanediol, 2,2-diethyl-1,3-propanediol, 2-methyl-2-propyl-1,3-propanediol, 2,4-dimethyl-2,4-pentanediol, 2,5-dimethyl-2,5-hexanediol, 5-hexene-1,2-diol, and 2-ethyl-1,3-hexanediol, and a mixture thereof.

The total amount of the one or more water-soluble solvents can vary but is typically about 1 to about 50 wt. %, based on the total weight of the hair coloring base composition. In some cases, the total amount of the one or more water-soluble solvents is about 1 to about 45 wt. %, about 1 to about 40 wt. %, about 1 to about 30 wt. %, about 1 to about 25 wt. %, about 5 to about 50 wt. %, about 5 to about 40 wt. %, about 5 to about 30 wt. %, about 5 to about 25 wt. %, about 10 to about 50 wt. %, about 10 to about 40 wt. %, about 10 to about 30 wt. %, or about 10 to about 25 wt. %, based on the total weight of the hair coloring base composition.

The total amount of water in the hair coloring base composition may vary but is typically about 5 to about 75 wt. %, based on the total weight of the hair coloring base composition. The total amount of water may be about 5 to about 75 wt. %, about 5 to about 70 wt. %, about 5 to about 65 wt. %, about 5 to about 60 wt. %, about 10 to about 75 wt. %, about 10 to about 70 wt. %, about 10 to about 65 wt. %, about 15 to about 75 wt. %, about 15 to about 70 wt. %, about 15 to about 65 wt. %, about 15 to about 60 wt. %, about 20 to about 75 wt. %, about 20 to about 70 wt. %, about 20 to about 65 wt. %, or about 20 to about 60 wt. %, based on the total weight of the hair coloring base composition.

The hair coloring base composition may optionally include one or more conditioning agents. Many conditioning agents are known, which may be useful. Nonetheless, in some instances, the hair coloring base compositions includes one or more glyceryl ethers as conditioning agent(s). Non-limiting examples of glyceryl ethers include glyceryl butyl ether, glyceryl isobutyl ether, glyceryl tert-butyl ether, glyceryl pentyl ether, glyceryl isopentyl ether, glyceryl hexyl ether, glyceryl isohexyl ether, glyceryl heptyl ether, glyceryl octyl ether, glyceryl ethylhexyl ether, glyceryl nonyl ether, glyceryl decyl ether, glyceryl isodecyl ether, glyceryl lauryl ether, glyceryl myristyl ether, glyceryl palmityl ether, glyceryl stearyl ether and glyceryl behenyl ether and their mixtures. Particularly useful glyceryl ethers also include glyceryl butyl ether, glyceryl isobutyl ether, glyceryl tert-butyl ether, glyceryl pentyl ether, glyceryl isopentyl ether, glyceryl hexyl ether, glyceryl isohexyl ether, glyceryl heptyl ether, glyceryl octyl ether, glyceryl ethylhexyl ether, glyceryl nonyl ether, glyceryl decyl ether, glyceryl isodecyl ether, glyceryl lauryl ether, and a mixture thereof. In some instances, glyceryl lauryl ether is particularly useful.

The total amount of the one or more conditioning agents, if present, may vary but is typically about 0.1 to about 15 wt. %, based on the total weight of the hair coloring base composition. The total amount of the one or more conditioning agents can be about 0.1 to about 12 wt. %, about 0.1 to about 10 wt. %, about 0.1 to about 8 wt. %, about 0.1 to about 6 wt. %, about 0.5 to about 15 wt. %, about 0.5 to about 12 wt. %, about 0.5 to about 10 wt. %, about 0.5 to about 8 wt. %, about 0.5 to about 6 wt. %, about 1 to about 15 wt. %, about 1 to about 12 wt. %, about 1 to about 10 wt. %, about 1 to about 8 wt. %, or about 1 to about 6 wt. %, based on the total weight of the hair coloring base composition.

The viscosity of the hair coloring base composition is typically about 25 to about 150 cps at 25° C. using a #1 spindle at 100 rpm. In some cases, the viscosity of the hair coloring base compositions may be about 20 to about 100 cps, about 50 to about 100 cps, about 60 to about 100 cps, about 70 to about 100 cps, about 50 to about 90 cps, about 50 to about 80 cps, or about 50 to about 75 cps at 25° C. using a #1 spindle at 100 rpm.

In one embodiment, the hair coloring base composition includes:
  about 0.001 to about 5 wt. % of one or more oxidative dye precursors, for example, one or more oxidative dye precursors selected from the group consisting of ortho- and/or para-aminophenols, ortho- and/or para-phenylenediamines, double bases, heterocyclic bases, acid addition salts thereof, and a mixture thereof;
  about 0.1 to about 25 wt. %, about 1 to about 20 wt. %, or about 1 to about 15 wt. % of one or more alkalizing agents, for example, one or more alkalizing agents selected from the group consisting of ammonia, ammonium hydroxide, monoethanolamine, sodium silicate, sodium metasilicate, and a mixture thereof; and in particular, ammonia, ammonium hydroxide, monethanolamine, or a mixture thereof;

about 0.01 to about 10 wt. %, about 0.01 to about 8, or about 0.1 to about 5 wt. % of one or more reducing agents, for example, one or more reducing agents selected from the group consisting of ammonium bisulfite, ammonium sulfite, potassium metabisulfite, potassium sulfite, sodium hydrosulfite, sodium metabisulfite, sodium sulfite, sodium bisulphite, thioglycolic acid, thiolactic acid, dehydroascorbic acid, a salt thereof, and a mixture thereof; and in particular thioglycolic acid, thiolactic acid, a salt thereof, and a mixture thereof, wherein the salts include those having a counter-ion such as an alkali metal, alkaline earth metal, or ammonium counter-ion;

optionally, about 0.1 to about 15 wt. %, about 0.1 to about 10, or about 0.1 to about 8 wt. % of one or more cationic conditioning polymers, for example, one or more cationic conditioning polymers selected from the group consisting of polyquaterniums;

about 0.1 to about 35 wt. % of one or more nonionic surfactants, for example, one or more nonionic surfactants selected from the group consisting of oxyethylenated amides, fatty alcohols, oxyethylenated fatty alcohols, and block-copolymer (polycondensate) surfactants of ethylene oxide and of propylene oxide, and a mixture thereof.

optionally, about 0.1 to about 15 wt. %, about 0.1 to about 10 wt. %, or about 1 to about 10 wt. % of one or more anionic surfactants, for example, one or more alkyl ether carboxylic acids, in particular, laureth-5 carboxylic acid;

optionally, about 0.1 to about 15 wt. %, about 0.1 to about 10 wt. %, or about 1 to about 10 wt. % of one or more conditioning agents, for example one or more glyceryl ethers, in particular, glyceryl lauryl ether;

about 1 to about 45 wt. % of one or more water-soluble solvents, for example, one or more water-soluble solvents selected from the group consisting of glycerin, alcohols, organic solvents, polyols, glycols, and a mixture thereof; and about 10 to about 70 wt. %, about 15 to about 65 wt. %, or about 20 to 60 wt. % of water;

wherein the weight percentages are based on the total weight of the hair coloring base composition.

The developer composition includes one or more oxidizing agents present in an amount sufficient to develop a color when mixed with a hair coloring base composition. Non-limiting examples of oxidizing agents include hydrogen peroxide, inorganic alkali metal peroxides (such as sodium periodate and sodium peroxide), organic peroxides (such as urea peroxide and melamine peroxide), inorganic perhydrate salts (such as the alkali metal salts of perborates, percarbonates, perphosphates, persilicates, persulfates), bromates, and a mixture thereof. In some cases, the developer composition includes hydrogen peroxide.

The total amount of the one or more oxidizing agents in the developer composition may vary, but is typically about 0.5 to about 50 wt. %, based on the total weight of the developer composition. In some instances, the total amount of the one or more oxidizing agents is about 0.5 to about 40 wt. %, about 1 to about 50 wt. %, about 1 to about 40 wt. %, about 1 to about 30 wt. %, about 1 to about 20 wt. %, about 1 to about 10 wt. %, about 5 to about 50 wt. %, about 5 to about 40 wt. %, about 5 to about 30 wt. %, about 5 to about 20 wt. %, or about 5 to about 10 wt. %, based on the total weight of the developer composition.

The developer composition typically includes one or more surfactants. The one or more surfactants may be anionic, amphoteric, non-ionic, zwitterionic, cationic surfactants, or a mixture thereof.

The total amount of the one or more surfactants in the developer composition can vary but is typically about 0.1 to about 25 wt. %, based on the total weight of the hair developer composition. The total amount of the one or more surfactants may be about 0.1 to about 20 wt. %, about 0.1 to about 15 wt. %, about 0.1 to about 10 wt. %, about 0.1 to about 5 wt. %, about 1 to about 25 wt. %, about 1 about 20 wt. %, about 1 to about 15 wt. %, about 1 to about 10 wt. %, or about 1 to about 5 wt. %, based on the total weight of the developer composition.

In some instances, the developer composition includes at least one or more nonionic surfactants. For example, the developer compositions may include one or more nonionic surfactants selected from the group consisting of oxyethylenated amides, fatty alcohols, oxyethylenated fatty alcohols, and mixture thereof. For example, the developer composition may include cetearyl alcohol (fatty alcohols), trideceth-2 carboxamide MEA (an oxyethylenated amide), and ceteareth-25 (an oxyethylenated fatty alcohol), or a mixture thereof.

Non-limiting examples of nonionic oxyethylenated amides are those of the following formula:

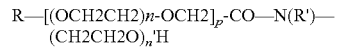

in which:

p denotes 0 or 1, n denotes a number ranging from 1 to 10 and preferably from 1 to 6, n' denotes a number ranging from 1 to 100 and preferably from 1 to 60, R' denotes a hydrogen atom or a CH2CH2OH radical and preferably a hydrogen atom, and R denotes a C10-C30 and preferably C12-C22 alkyl or alkenyl radical.

Examples of these compounds include AMIDET A15 sold by the company Kao (INCI name: Trideceth-2 carboxamide MEA), ETHOMID HP 60 sold by the company Akzo Nobel (INCI name: PEG-50 Hydrogenated Palmamide) and AMIDET N sold by the company Kao (INCI name: PEG-4 Rapeseedamide). In some cases, trideceth-2 carboxamide MEA may be particularly useful.

Non-limiting examples of fatty alcohols include saturated or unsaturated and linear or branched alcohols comprising from 6 to 30 carbon atoms and preferably from 8 to 30 carbon atoms, for instance, cetyl alcohol, isostearyl alcohol, stearyl alcohol and the mixture thereof (cetylstearyl alcohol/cetearyl alcohol), octyldodecanol, 2-butyloctanol, 2-hexyldecanol, 2-undecylpentadecanol, oleyl alcohol, linolenyl alcohol, ricinoleyl alcohol, undecylenyl alcohol and linoleyl alcohol, and mixtures thereof. In some cases, cetylstearyl/cetearyl alcohol may be particularly useful.

Non-limiting examples of oxyethylenated fatty alcohols include those comprising less than 10 OE units, preferably chosen from oxyethylenated derivatives of saturated or unsaturated, linear or branched, preferably linear, $C_8$-$C_{30}$ and preferably $C_{12}$-$C_{22}$ fatty alcohols, for instance cetyl alcohol, oleyl alcohol, oleocetyl alcohol, lauryl alcohol, behenyl alcohol, cetearyl alcohol, stearyl alcohol and isostearyl alcohol, and mixtures thereof.

The oxyethylenated fatty alcohols may have an average degree of ethoxylation of 2 to 29. Non-limiting examples of oxyethylenated fatty alcohols having an average degree of ethoxylation of 2 to 29 are, for example, laureth-2, oleth-2, ceteareth-2, laneth-2, laureth-3, oleth-3, ceteareth-3, laureth-4, oleth-4, ceteareth-4, laneth-4, laureth-5, oleth-5, ceteareth-5, laneth-5, deceth-4, deceth-7, laureth-7, oleth-7, coceth-7, ceteth-7, ceteareth-7, C11-15 pareth-7, laureth-9, oleth-9, ceteareth-9, laureth-10, oleth-10, beheneth-10, ceteareth-10, laureth-12, ceteareth-12, trideceth-12, ceteth-15, laneth-15, ceteareth-15, laneth-16, ceteth-16, oleth-16, steareth-16, oleth-20, ceteth-20, ceteareth-20, laneth-20, steareth-21, ceteareth-23, ceteareth-25, ceteareth-27, and a mixture thereof.

The developer compositions may be free or essentially free of amphoteric surfactants and/or the developer compositions may be free or essentially free of cationic surfactants and/or the developer compositions may be free or essentially free of anionic surfactants.

The total amount of the one or more nonionic surfactants in the developer composition can vary but is typically about 0.1 to about 25 wt. %, based on the total weight of the hair developer composition. The total amount of the one or more nonionic surfactants may be about 0.1 to about 20 wt. %, about 0.1 to about 15 wt. %, about 0.1 to about 10 wt. %, about 0.1 to about 5 wt. %, about 1 to about 25 wt. %, about 1 about 20 wt. %, about 1 to about 15 wt. %, about 1 to about 10 wt. %, or about 1 to about 5 wt. %, based on the total weight of the developer composition.

The developer composition may include one or more water-soluble solvents. Non-limiting examples of water-soluble solvents include, for example, glycerin, alcohols (for example, $C_{1-30}$, $C_{1-15}$, $C_{1-10}$, or $C_{1-4}$ alcohols), organic solvents, polyols, glycols, and a mixture thereof. The water-soluble solvents useable in the developer composition include those discussed above with respect to the hair coloring base composition, which for the sake of brevity are not reiterated here.

The total amount of the one or more water-soluble solvents in the developer composition, if present, may be about 0.1 to about 25 wt. %, about 0.1 to about 20 wt. %, about 0.1 to about 15 wt. %, about 0.1 to about 10 wt. %, or about 0.1 to about 5 wt. %, based on the total weight of the developer composition.

The viscosity of the developer composition is typically about 250 to about 2000 cps at 25° C. using a #4 spindle at 100 rpm. In some cases, the viscosity of the developer composition may be about 500 to about 2500 cps, about 500 to about 2000 cps, about 500 to about 1500 cps, about 600 to about 1300 cps, or about 650 to about 1200 cps at 25° C. using a #4 spindle at 100 rpm.

In one embodiment, the developer composition includes:
  about 1 to about 40 wt. %, about 1 to about 25 wt. %, or about 1 to about 15 wt. % of one or more oxidizing agents, for example, one or more oxidizing agents selected from the group consisting of hydrogen peroxide, inorganic alkali metal peroxides (such as sodium periodate and sodium peroxide), organic peroxides (such as urea peroxide and melamine peroxide), inorganic perhydrate salts (such as the alkali metal salts of perborates, percarbonates, perphosphates, persilicates, persulphates), bromates, and a mixture thereof;
  about 0.1 to about 20 wt. %, about 0.1 to about 10 wt. %, or about 1 to about 10 wt. % of one or more nonionic surfactants, for example, one or more nonionic surfactants selected from the group consisting of oxyethylenated amides, fatty alcohols, oxyethylenated fatty alcohols, and a mixture thereof;
  optionally, about 0.1 to about 25 wt. %, about 0.1 to about 15 wt. %, or about 0.1 to about 10 wt. % of one or more water-soluble solvents, for example, glycerin, alcohols, organic solvents, polyols, glycols, and a mixture thereof; and
  about 50 to about 92 wt. %, about 60 to about 92 wt. %, or about 75 to about 90 wt. % of water;
    wherein the weight percentages are based on the total weight of the developer composition.

The hair coloring base composition and the developer composition can be mixed at a ratio of about 1:5 to about 5:1 (hair coloring base composition:developer composition). In some cases, the ratio is about 1:4 to about 4:1, about 1:3 to about 3:1, about 1:2 to about 2:1, or about 1:1 (hair coloring base composition:developer composition).

As mentioned previously, one or more hair coloring base compositions and one or more developer compositions can be incorporated into a cartridge having individual packets (or chambers) for receiving the compositions, wherein each of the individual compositions are separately contained in the packets or chambers. The cartridges may be used with or included as part of a hair coloring device or appliance. For example, a hair coloring device or appliance may include a cartridge according to the instant disclosure, a portal member capable of receiving or of attachment to the cartridge; a brushhead/dispenser member attached to the device or appliance and, for example, in fluid communication with the chambers or packets of the cartridge; wherein the one or more hair coloring base compositions and the one or more developer compositions in the cartridge are directed from the cartridge to the brushhead/dispenser by a user operating on the receptacle assembly or by a pump operating on the device or appliance.

The cartridge, or the device or appliance, may be structurally sized and adapted for multiple use, or single use (and optionally disposable by the user after a single use). Furthermore, the chambers or packets of the cartridge may be sized to hold an amount of hair coloring base composition(s) and/or developer composition(s) for one hair coloring event (a single use), but may also be sized to hold an amount of hair coloring base composition(s) and/or developer composition(s) for multiple coloring events (multiple uses), and may be adapted to be refilled after one or more uses.

The brushhead of a hair coloring device or appliance may have a plurality of tines comprising openings at the distal end of the tines, such that an active hair coloring composition may be dispensed from the tines onto the hair. Furthermore, the plurality of tines may separately or additional have openings along the lengths thereof for expelling active hair coloring composition. In addition to a plurality of tines, the device or appliance may include bristle tufts located between the tines, or in addition nearby the tines, the bristle tufts extending slightly beyond the tines, acting as a standoff for the tines from the scalp.

In some instances, the cartridge and/or the device or appliance may include a flexible housing so that a user, upon application of a squeeze force to the housing forces active coloring composition therein into the brushhead. Also, the hair coloring device or appliance may include one or more pumps driven by one or more motors for moving one or more hair coloring base compositions and one or more developer compositions from the chambers or packets of the cartridge in which the compositions are contained, to the brushhead/dispenser. Additionally, the hair coloring device or appliance may include a driving assembly for moving the brushhead/dispenser in a lateral direction back and forth. The distance of lateral movement may be, for example, greater than one half the distance between adjacent tines but no greater than twice the distance between adjacent tines.

The hair coloring device or appliance may also include a mixer assembly and an interface member for connecting to the cartridge, the interface member including a valve for controlling the movement of one or more hair coloring base compositions and the one or more developer compositions from their respective chambers or packets to the mixer assembly where the one or more hair coloring base compositions is combined with the one or more developer compositions. Hair coloring assemblies, devices, and appliances are disclosed in US2016/0166032, US2016/0143408, and US2016/0183664, the content of which is incorporated herein by reference in its entirety.

The instant disclosure also encompasses methods for coloring hair. For example, a method for coloring hair using assemblies, devices or appliances comprising the hair coloring base composition(s) and the developer composition(s), such as those described herein. Such methods may comprise obtaining a cartridge, device or appliance, operating it to form an active hair coloring composition, and dispensing or applying the active hair coloring composition to hair.

The active hair coloring composition may be applied to the hair and allowed to remain on the hair for a period of time, for example, a period of time sufficient for imparting a color change to the hair. The amount of time will vary depending on a variety of factors. Darker and coarser hair typically requires more time than lighter and softer hair. Other factors that influence the amount of time include the strength of the developer composition, the degree of color change desired, and the sensitivity of the individual's scalp to the chemicals in the active hair coloring composition. In general, the active hair coloring composition is allowed to remain on the hair for about 5 minutes to about 2 hours. In some instances, the active hair coloring composition is allowed to remain on the hair from about 5 minutes to about 1.5 hours, about 5 minutes to about 1 hour, about 5 minutes to about 45 minutes, about 5 minutes to about 30 minutes, about 5 minutes to about 20 minutes, about 5 minutes to about 15 minutes, about 10 minutes to about 2 hours about 10 minutes to about 1.5 hours, about 10 minutes to about 1 hour, about 10 minutes to about 45 minutes, or about 10 minutes to about 30 minutes. After the active hair coloring composition is allowed to remain on the hair for a period of time, it is typically rinsed from the hair with water. Upon rinsing, the hair may also be shampooed and/or conditioned with a shampoo and/or conditioner.

More exhaustive but non-limiting lists of components useful in the antioxidants compositions of the instant disclosure are provided below.

Oxidation Dye Precursors

The oxidation dyes are generally chosen from one or more oxidation bases optionally combined with one or more couplers. By way of example, the oxidation bases are chosen from para-phenylenediamines, bis(phenyl)alkylenediamines, para-aminophenols, ortho-aminophenols and heterocyclic bases, and the addition salts thereof.

Among the para-phenylenediamines that may be mentioned, for example, are para-phenylenediamine, para-toluenediamine, 2-chloro-para-phenylenediamine, 2,3-dimethyl-para-phenylenediamine, 2,6-dimethyl-para-phenylenediamine, 2,6-diethyl-para-phenylenediamine, 2,5-dimethyl-para-phenylenediamine, N,N-dimethyl-para-phenylenediamine, N,N-diethyl-para-phenylenediamine, N,N-dipropyl-para-phenylenediamine, 4-amino-N,N-diethyl-3-methylaniline, N,N-bis(.beta.-hydroxyethyl)-para-phenylenediamine, 4-N,N-bis(.beta.-hydroxyethyl)amino-2-methylaniline, 4-N,N-bis(.beta.-hydroxyethyl)amino-2-chloroaniline, 2-.beta.-hydroxyethyl-para-phenylenediamine, 2-methoxymethyl-para-phenylenediamine, 2-fluoro-para-phenylenediamine, 2-isopropyl-para-phenylenediamine, N-(.beta.-hydroxypropyl)-para-phenylenediamine, 2-hydroxymethyl-para-phenylenediamine, N,N-dimethyl-3-methyl-para-phenylenediamine, N-ethyl-N-(.beta.-hydroxyethyl)-para-phenylenediamine, N-(.beta.,.gamma.-dihydroxypropyl)-para-phenylenediamine, N-(4'-aminophenyl)-para-phenylenediamine, N-phenyl-para-phenylenediamine, 2-.beta.-hydroxyethyloxy-para-phenylenediamine, 2-.beta.-acetylaminoethyloxy-para-phenylenediamine, N-(.beta.-methoxyethyl)-para-phenylenediamine, 4-aminophenylpyrrolidine, 2-thienyl-para-phenylenediamine, 2-.beta.-hydroxyethylamino-5-aminotoluene and 3-hydroxy-1-(4'-aminophenyl)pyrrolidine, and the addition salts thereof with an acid.

Among the para-phenylenediamines mentioned above, para-phenylenediamine, para-toluenediamine, 2-isopropyl-para-phenylenediamine, 2-.beta.-hydroxyethyl-para-phenylenediamine, 2-.beta.-hydroxyethyloxy-para-phenylenediamine, 2,6-dimethyl-para-phenylenediamine, 2,6-diethyl-para-phenylenediamine, 2,3-dimethyl-para-phenylenediamine, N,N-bis(.beta.-hydroxyethyl)-para-phenylenediamine, 2-chloro-para-phenylenediamine and 2-.beta.-acetylaminoethyloxy-para-phenylenediamine, and the addition salts thereof with an acid, are particularly preferred.

Among the bis(phenyl)alkylenediamines that may be mentioned, for example, are N,N'-bis(.beta.-hydroxyethyl)-N,N-bis(4'-aminophenyl)-1,3-diaminopropanol, N,N'-bis(.beta.-hydroxyethyl)-N,N'-bis(4'-aminophenyl)ethylenediamine, N,N'-bis(4-aminophenyl)tetramethylenediamine, N,N'-bis(.beta.-hydroxyethyl)-N, N'-bis(4-aminophenyl)tetramethylenediamine, N,N'-bis(4-methylaminophenyl)tetramethylenediamine, N,N'-bis(ethyl)-N,N'-bis(4'-amino-3'-methylphenyl)ethylenediamine and 1,8-bis(2,5-diaminophenoxy)-3,6-dioxaoctane, and the addition salts thereof.

Among the para-aminophenols that may be mentioned, for example, are para-aminophenol, 4-amino-3-methylphenol, 4-amino-3-fluorophenol, 4-amino-3-chlorophenol, 4-amino-3-hydroxymethylphenol, 4-amino-2-methylphenol, 4-amino-2-hydroxymethylphenol, 4-amino-2-methoxymethylphenol, 4-amino-2-aminomethylphenol, 4-amino-2-(.beta.-hydroxyethylaminomethyl)phenol and 4-amino-2-fluorophenol, and the addition salts thereof with an acid.

Among the ortho-aminophenols that may be mentioned, for example, are 2-aminophenol, 2-amino-5-methylphenol, 2-amino-6-methylphenol and 5-acetamido-2-aminophenol, and the addition salts thereof.

Among the heterocyclic bases that may be mentioned, for example, are pyridine derivatives, pyrimidine derivatives and pyrazole derivatives.

Among the pyridine derivatives that may be mentioned are the compounds such as 2,5-diaminopyridine, 2-(4-methoxyphenyl)amino-3-aminopyridine and 3,4-diaminopyridine, and the addition salts thereof. Other pyridine oxidation bases that are useful in the present disclosure are the 3-aminopyrazolo[1,5-a]pyridine oxidation bases or the addition salts thereof described, for example, in patent application FR 2 801 308. Examples that may be mentioned include pyrazolo[1,5-a]pyrid-3-ylamine, 2-acetylaminopyrazolo[1,5-a]pyrid-3-ylamine, 2-morpholin-4-ylpyrazolo[1,5-a]pyrid-3-ylamine, 3-aminopyrazolo[1,5-a]pyridine-2-carboxylic acid, 2-methoxypyrazolo[1,5-a]pyrid-3-ylamine, (3-aminopyrazolo[1,5-a]pyrid-7-yl)methanol, 2-(3-aminopyrazolo[1,5-a]pyrid-5-yl)ethanol, 2-(3-aminopyrazolo[1,5-a]pyrid-7-yl)ethanol, (3-aminopyrazolo[1,5-a]pyrid-2-yl) methanol, 3,6-diaminopyrazolo[1,5-a]pyridine, 3,4-diaminopyrazolo[1,5-a]pyridine, pyrazolo[1,5-a]pyridine-3,7-diamine, 7-morpholin-4-ylpyrazolo[1,5-a]pyrid-3-ylamine, pyrazolo[1,5-a]pyridine-3,5-diamine, 5-morpholin-4-ylpyrazolo[1,5-a]pyrid-3-ylamine, 2-[(3-aminopyrazolo[1,5-a]pyrid-5-yl)(2-hydroxyethyl)amino] ethanol, 2-[(3-aminopyrazolo[1,5-a]pyrid-7-yl)(2-hydroxyethyl)amino]ethanol, 3-aminopyrazolo[1,5-a]pyridin-5-ol, 3-aminopyrazolo[1,5-a]pyridin-4-ol, 3-aminopyrazolo[1,5-a]pyridin-6-ol, 3-aminopyrazolo[1,5-a]pyridin-7-ol, 2-.quadrature.-hydroxyethoxy-3-amino-pyrazolo[1,5-a] pyridine; 2-(4-dimethylpyperazinium-1-yl)-3-amino-pyrazolo[1,5-a]pyridine; and the addition salts thereof.

More particularly oxidation bases that are useful in the present disclosure are selected from 3-aminopyrazolo-[1,5-a]-pyridines and preferably substituted on carbon atom 2 by:

(a) one (di)(C1-C6)(alkyl)amino group wherein said alkyl group can be substituted by at least one hydroxy, amino, imidazolium group;

(b) one heterocycloalkyl group containing from 5 to 7 members chain, and from 1 to 3 heteroatoms, potentially cationic, potentially substituted by one or more ($C_1$-$C_6$-alkyl, such as di(C1-C4)alkylpiperazinium; or (c) one ($C_1$-$C_6$)alkoxy potentially substituted by one or more hydroxy groups such as .quadrature.-hydroxyalkoxy, and the addition salts thereof.

Among the pyrimidine derivatives that may be mentioned are compounds such as 2,4,5,6-tetraaminopyrimidine, 4-hydroxy-2,5,6-triaminopyrimidine, 2-hydroxy-4,5,6-triaminopyrimidine, 2,4-dihydroxy-5,6-diaminopyrimidine, 2,5,6-triaminopyrimidine and their addition salts and their tautomeric forms, when a tautomeric equilibrium exists.

Among the pyrazole derivatives that may be mentioned are compounds such as 4,5-diamino-1-methyl-pyrazole, 4,5-diamino-1-(.beta.-hydroxyethyl)pyrazole, 3,4-diaminopyrazole, 4,5-diamino-1-(4'-chlorobenzyl)pyrazole, 4,5-diamino-1,3-dimethylpyrazole, 4,5-diamino-3-methyl-1-phenyl-pyrazole, 4,5-diamino-1-methyl-3-phenylpyrazole, 4-amino-1,3-dimethyl-5-hydrazinopyrazole, 1-benzyl-4,5-diamino-3-methyl-pyrazole, 4,5-diamino-3-tert-butyl-1-methylpyrazole, 4,5-diamino-1-tert-butyl-3-methylpyrazole, 4,5-diamino-1-(beta.-hydroxyethyl)-3-methylpyrazole, 4,5-diamino-1-ethyl-3-methylpyrazole, 4,5-diamino-1-ethyl-3-(4'-methoxyphenyl)pyrazole, 4,5-diamino-1-ethyl-3-hydroxymethylpyrazole, 4,5-diamino-3-hydroxymethyl-1-methylpyrazole, 4,5-diamino-3-hydroxymethyl-1-isopropylpyrazole, 4,5-diamino-3-methyl-1-isopropylpyrazole, 4-amino-5-(2'-aminoethyl)amino-1,3-dimethylpyrazole, 3,4,5-triaminopyrazole, 1-methyl-3,4,5-triaminopyrazole, 3,5-diamino-1-methyl-4-methylaminopyrazole, 3,5-diamino-4-(.beta.-hydroxyethyl)amino-1-methylpyrazole, and the addition salts thereof. 4,5-Diamino-1-(.beta.-methoxyethyl)pyrazole may also be used.

Pyrazole derivatives that may also be mentioned include diamino-N,N-dihydropyrazolopyrazolones such as the following compounds and the addition salts thereof: 2,3-diamino-6,7-dihydro-1H,5H-pyrazolo[1,2-a]pyrazol-1-one, 2-amino-3-ethylamino-6,7-dihydro-1H,5H-pyrazolo[1,2-a] pyrazol-1-one, 2-amino-3-isopropylamino-6,7-dihydro-1H, 5H-pyrazolo[1,2-a]pyrazol-1-one, 2-amino-3-(pyrrolidin-1-yl)-6,7-dihydro-1H,5H-pyrazolo[1,2-a]pyrazol-1-one, 4,5-diamino-1,2-diethyl-1,2-dihydropyrazol-3-one, 4,5-diamino-1,2-diethyl-1,2-dihydropyrazol-3-one, 4,5-diamino-1,2-di-(2-hydroxyethyl)-1,2-dihydropyrazol-3-one, 2-amino-3-(2-hydroxyethyl)amino-6,7-dihydro-1H, 5H-pyrazolo[1,2-a]pyrazol-1-one, 2-amino-3-dimethyl-amino-6,7-dihydro-1H,5H-pyrazolo[1,2-a]pyrazol-1-one, 2,3-diamino-5,6,7,8-tetrahydro-1H,6H-pyridazino[1,2-a] pyrazol-1-one, 4-amino-1,2-diethyl-5-(pyrrolidin-1-yl)-1,2-dihydropyrazol-3-one, 4-amino-5-(3-dimethylaminopyrrolidin-1-yl)-1,2-diethyl-1,2-dihydropyrazol-3-one, 2,3-diamino-6,7-dihydroxy-6,7-dihydro-1H,5H-pyrazolo[1,2-a] pyrazol-1-one. 2,3-Diamino-6,7-dihydro-1H,5H-pyrazolo [1,2-a]pyrazol-1-one and/or a salt thereof will preferably be used. 4,5-Diamino-1-(.beta.-hydroxyethyl)pyrazole and/or 2,3-diamino-6,7-dihydro-1H,5H-pyrazolo[1,2-a]pyrazol-1-one and/or a salt thereof will preferentially be used as heterocyclic bases.

Couplers

The couplers include those conventionally used in oxidative methods of coloring hair, for example, meta-aminophenols, meta-phenylenediamines and meta-diphenols, naphthols, mono- or polyhydroxylated naphthalene derivatives, and heterocyclic couplers such as, for example, indole derivatives, indoline derivatives, sesamol and its derivatives, pyridine derivatives, pyrazolotriazole derivatives, pyrazolones, indazoles, benzimidazoles, benzothiazoles, benzoxazoles, 1,3-benzodioxoles, quinolines, benzomorpholine derivatives, pyrazoloazole derivatives, pyrroloazole derivatives, imidazoloazole derivatives, pyrazolopyrimidine derivatives, pyrazoline-3,5-dione derivatives, pyrrolo[3,2-d] oxazole derivatives, pyrazolo[3,4-d]thiazole derivatives, thiazoloazole S-oxide derivatives, thiazoloazole S,S-dioxide derivatives, and the acid addition salts thereof.

Suitable color couplers include, for example, those having the following general formula:

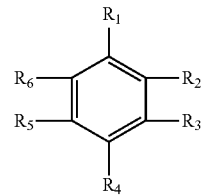

wherein $R_1$ is unsubstituted hydroxy or amino, or hydroxy or amino substituted with one or more $C_{1-6}$ hydroxyalkyl groups, $R_3$ and $R_5$ are each independently hydrogen, hydroxy, amino, or amino substituted with $C_{1-6}$ alkyl, $C_{1-6}$ alkoxy, or $C_{1-6}$ hydroxyalkyl group; and $R_2$, $R_4$, and $R_6$ are each independently hydrogen, $C_{1-6}$ alkoxy, $C_{1-6}$ hydroxyalkyl, or $C_{1-6}$ alkyl, or $R_3$ and $R_4$ together may form a methylenedioxy or ethylenedioxy group. Examples of such compounds include meta-derivatives such as phenols, meta-aminophenols, meta-phenylenediamines, and the like, which may be unsubstituted, or substituted on the amino group or benzene ring with alkyl, hydroxyalkyl, alkylamino groups, and the like. Suitable couplers include m-aminophenol, 2,4-diaminotoluene, 4-amino, 2-hydroxytoluene, phenyl methyl pyrazolone, 3,4-methylenedioxyphenol, 3,4-methylenedioxy-1-[(beta-hydroxyethyl)amino]benzene, 1-methoxy-2-amino-4-[(beta-hydroxyethyl)amino]benzene, 1-hydroxy-3-(dimethylamino)benzene, 6-methyl-1-hydroxy-3[(beta-hydroxyethyl)amino]benzene, 2,4-dichloro-1-hydroxy-3-aminobenzene, 1-hydroxy-3-(diethylamino) benzene, 1-hydroxy-2-methyl-3-aminobenzene, 2-chloro-6-methyl-1-hydroxy-3-aminobenzene, 1,3-diaminobenzene, 6-methoxy-1,3-diaminobenzene, 6-hydroxyethoxy-1,3-diaminobenzene, 6-methoxy-5-ethyl-1,3-diaminobenzene, 6-ethoxy-1,3-diaminobenzene, 1-bis(beta-hydroxyethyl)

amino-3-aminobenzene, 2-methyl-1, 3-diaminobenzene, 6-methoxy-1-amino-3-[(beta-hydroxyethyl)amino]-benzene, 6-(beta-aminoethoxy)-1,3-diaminobenzene, 6-(beta-hydroxyethoxy)-1-amino-3-(methylamino)benzene, 6-carboxymethoxy-1,3-diaminobenzene, 6-ethoxy-1-bis(beta-hydroxyethyl)amino-3-aminobenzene, 6-hydroxyethyl-1,3-diaminobenzene, 1-hydroxy-2-isopropyl-5-methylbenzene, 1,3-dihydroxybenzene, 2-chloro-1,3-dihydroxybenzene, 2-methyl-1,3-dihydroxybenzene, 4-chloro-1,3-dihydroxybenzene, 5,6-dichloro-2-methyl-1, 3-dihydroxybenzene, 1-hydroxy-3-amino-benzene, 1-hydroxy-3-(carbamoylmethylamino)benzene, 6-hydroxybenzomorpholine, 4-methyl-2,6-dihydroxypyridine, 2,6-dihydroxypyridine, 2,6-diaminopyridine, 6-aminobenzomorpholine, 1-phenyl-3-methyl-5-pyrazolone, 1-hydroxynaphthalene, 1,7-dihydroxynaphthalene, 1,5-dihydroxynaphthalene, 5-amino-2-methyl phenol, 4-hydroxyindole, 4-hydroxyindoline, 6-hydroxyindole, 6-hydroxyindoline, 2,4-diamionphenoxyethanol, and mixtures thereof.

Other couplers may be chosen, for example, from 2,4-diamino-1-(β-hydroxyethyloxy)benzene, 2-methyl-5-aminophenol, 5-N-(β-hydroxyethyl) amino-2-methylphenol, 3-aminophenol, 1,3-dihydroxybenzene, 1,3-dihydroxy-2-methylbenzene, 4-chloro-1,3-dihydroxybenzene, 2,4-diamino 1-(β-hydroxyethyloxy) benzene, 2-amino-4-(β-hydroxyethylamino)-1-methoxybenzene, 1,3-diaminobenzene, 1,3-bis(2,4-diaminophenoxy)propane, sesamol, 1-amino-2-methoxy-4,5-methylenedioxybenzene, α-naphthol, 6-hydroxyindole, 4-hydroxyindole, 4-hydroxy-N-methylindole, 6-hydroxyindoline, 2,6-dihydroxy-4-methylpyridine, 1H-3-methylpyrazol-5-one, 1-phenyl-3-methylpyrazol-5-one, 2-amino-3-hydroxypyridine, 3,6-dimethylpyrazolo[3,2-c]-1,2,4-triazole, 2, 6-dimethylpyrazolo[1,5-b]-1,2,4-triazole, 6-methyl pyrazolo[1,5-a]-benzimidazole, and the acid addition salts thereof.

In one embodiment, the couplers include resorcinol, 1-naphthol, 2-methylresorcinol, 4-amino-2-hydroxy toluene, m-aminophenol, 2,4-diaminophenoxyethanol, phenyl methyl pyrazolone, hydroxybenzomorpholine, 2-methyl-5-hydroxyetylaminophenol, 6-hydroxyindole, 2-amino-3-hydroxypyridine, 5-amino-6-chloro-o-cresol, 4-chlororesorcinol, their salts, and mixtures thereof.

In general, the acid addition salts of the oxidation bases and couplers may be chosen from hydrochlorides, hydrobromides, sulfates, tartrates, lactates, and acetates.

Non-Ionic Surfactants

Nonionic surfactants are compounds well known in themselves (see, e.g., in this regard, "Handbook of Surfactants" by M. R. Porter, Blackie & Son publishers (Glasgow and London), 1991, pp. 116-178), which is incorporated herein by reference in its entirety.

The nonionic surfactant can be, for example, selected from alcohols, alpha-diols, alkylphenols and esters of fatty acids, these compounds being ethoxylated, propoxylated or glycerolated and having at least one fatty chain comprising, for example, from 8 to 18 carbon atoms, it being possible for the number of ethylene oxide or propylene oxide groups to range from 2 to 50, and for the number of glycerol groups to range from 1 to 30. Maltose derivatives may also be mentioned. Non-limiting mention may also be made of copolymers of ethylene oxide and/or of propylene oxide; condensates of ethylene oxide and/or of propylene oxide with fatty alcohols; polyethoxylated fatty amides comprising, for example, from 2 to 30 mol of ethylene oxide; polyglycerolated fatty amides comprising, for example, from 1.5 to 5 glycerol groups, such as from 1.5 to 4; ethoxylated fatty acid esters of sorbitan comprising from 2 to 30 mol of ethylene oxide; ethoxylated oils from plant origin; fatty acid esters of sucrose; fatty acid esters of polyethylene glycol; polyethoxylated fatty acid mono or diesters of glycerol ($C_6$-$C_{24}$)alkylpolyglycosides; N-($C_6$-$C_{24}$)alkylglucamine derivatives, amine oxides such as ($C_{10}$-$C_{14}$)alkylamine oxides or N—($C_{10}$-$C_{14}$)acylaminopropylmorpholine oxides; and a mixture thereof.

The nonionic surfactants may preferably be chosen from polyoxyalkylenated or polyglycerolated nonionic surfactants. The oxyalkylene units are more particularly oxyethylene or oxypropylene units, or a combination thereof, and are preferably oxyethylene units.

Examples of oxyalkylenated nonionic surfactants that may be mentioned include: oxyalkylenated ($C_8$-$C_{24}$)alkylphenols, saturated or unsaturated, linear or branched, oxyalkylenated $C_8$-$C_{30}$ alcohols, saturated or unsaturated, linear or branched, oxyalkylenated $C_8$-$C_{30}$ amides, esters of saturated or unsaturated, linear or branched, $C_8$-$C_{30}$ acids and of polyethylene glycols, polyoxyalkylenated esters of saturated or unsaturated, linear or branched, $C_8$-$C_{30}$ acids and of sorbitol, saturated or unsaturated, oxyalkylenated plant oils, condensates of ethylene oxide and/or of propylene oxide, inter alia, alone or as mixtures.

The surfactants preferably contain a number of moles of ethylene oxide and/or of propylene oxide of between 2 and 100 and most preferably between 2 and 50.

In accordance with one preferred embodiment of the invention, the oxyalkylenated nonionic surfactants are chosen from oxyethylenated $C_8$-$C_{30}$ alcohols.

Examples of ethoxylated fatty alcohols (or $C_8$-$C_{30}$ alcohols) that may be mentioned include the adducts of ethylene oxide with lauryl alcohol, especially those containing from 9 to 50 oxyethylene groups and more particularly those containing from 10 to 25 oxyethylene groups (Laureth-10 to Laureth-25); the adducts of ethylene oxide with behenyl alcohol, especially those containing from 9 to 50 oxyethylene groups (Beheneth-9 to Beheneth-50); the adducts of ethylene oxide with cetearyl alcohol (mixture of cetyl alcohol and stearyl alcohol), especially those containing from 10 to 30 oxyethylene groups (Ceteareth-10 to Ceteareth-30); the adducts of ethylene oxide with cetyl alcohol, especially those containing from 10 to 30 oxyethylene groups (Ceteth-10 to Ceteth-30); the adducts of ethylene oxide with stearyl alcohol, especially those containing from 10 to 30 oxyethylene groups (Steareth-10 to Steareth-30); the adducts of ethylene oxide with isostearyl alcohol, especially those containing from 10 to 50 oxyethylene groups (Isosteareth-10 to Isosteareth-50); and a mixture thereof.

As examples of polyglycerolated nonionic surfactants, polyglycerolated $C_8$-$C_{40}$ alcohols are preferably used.

In particular, the polyglycerolated $C_8$-$C_{40}$ alcohols correspond to the following formula:

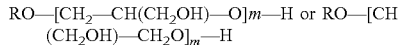

in which R represents a linear or branched $C_8$-$C_{40}$ and preferably $C_8$-$C_{30}$ alkyl or alkenyl radical, and m represents a number ranging from 1 to 30 and preferably from 1.5 to 10.

As examples of compounds that are suitable in the context of the invention, mention may be made of lauryl alcohol containing 4 mol of glycerol (INCI name: Polyglyceryl-4 Lauryl Ether), lauryl alcohol containing 1.5 mol of glycerol, oleyl alcohol containing 4 mol of glycerol (INCI name: Polyglyceryl-4 Oleyl Ether), oleyl alcohol containing 2 mol of glycerol (INCI name: Polyglyceryl-2 Oleyl Ether), cetearyl alcohol containing 2 mol of glycerol, cetearyl alcohol containing 6 mol of glycerol, oleocetyl alcohol containing 6 mol of glycerol, and octadecanol containing 6 mol of glycerol.

The alcohol may represent a mixture of alcohols in the same way that the value of m represents a statistical value, which means that, in a commercial product, several species of polyglycerolated fatty alcohol may coexist in the form of a mixture.

According to one of the embodiments according to the present invention, the nonionic surfactant may be selected from esters of polyols with fatty acids with a saturated or unsaturated chain containing for example from 8 to 24 carbon atoms, preferably 12 to 22 carbon atoms, and alkoxylated derivatives thereof, preferably with a number of alkyleneoxide of from 10 to 200, and more preferably from 10 to 100, such as glyceryl esters of a $C_8$-$C_{24}$, preferably $C_{12}$-$C_{22}$, fatty acid or acids and alkoxylated derivatives thereof, preferably with a number of alkyleneoxide of from 10 to 200, and more preferably from 10 to 100; polyethylene glycol esters of a $C_8$-$C_{24}$, preferably $C_{12}$-$C_{22}$, fatty acid or acids and alkoxylated derivatives thereof, preferably with a number of alkyleneoxide of from 10 to 200, and more preferably from 10 to 100; sorbitol esters of a $C_8$-$C_{24}$, preferably $C_{12}$-$C_{22}$, fatty acid or acids and alkoxylated derivatives thereof, preferably with a number of alkyleneoxide of from 10 to 200, and more preferably from 10 to 100; sugar (sucrose, glucose, alkylglycose) esters of a $C_8$-$C_{24}$, preferably $C_{12}$-$C_{22}$, fatty acid or acids and alkoxylated derivatives thereof, preferably with a number of alkyleneoxide of from 10 to 200, and more preferably from 10 to 100; ethers of fatty alcohols; ethers of sugar and a $C_8$-$C_{24}$, preferably $C_{12}$-$C_{22}$, fatty alcohol or alcohols; and a mixture thereof.

Examples of ethoxylated fatty esters that may be mentioned include the adducts of ethylene oxide with esters of lauric acid, palmitic acid, stearic acid or behenic acid, and a mixture thereof, especially those containing from 9 to 100 oxyethylene groups, such as PEG-9 to PEG-50 laurate; PEG-9 to PEG-50 palmitate; PEG-9 to PEG-50 stearate; PEG-9 to PEG-50 palmitostearate; PEG-9 to PEG-50 behenate; polyethylene glycol 100 EO monostearate; and a mixture thereof.

As glyceryl esters of fatty acids, glyceryl stearate (glyceryl mono-, di- and/or tristearate) (glyceryl stearate) or glyceryl ricinoleate and a mixture thereof can in particular be cited.

As glyceryl esters of $C_8$-$C_{24}$ alkoxylated fatty acids, polyethoxylated glyceryl stearate (glyceryl mono-, di- and/or tristearate) such as PEG-20 glyceryl stearate can for example be cited.

Mixtures of these surfactants, such as for example the product containing glyceryl stearate and PEG-100 stearate, marketed under the name ARLACEL 165 by Croda, and a product containing glyceryl stearate (glyceryl mono- and distearate) and potassium stearate, can also be used.

The sorbitol esters of $C_8$-$C_{24}$ fatty acids and alkoxylated derivatives thereof can be selected from sorbitan palmitate, sorbitan trioleate and esters of fatty acids and alkoxylated sorbitan containing for example from 20 to 100 EO, such as for example polyethylene sorbitan trioleate (polysorbate 85) or the compounds marketed under the trade names Tween 20 or Tween 60 by Croda.

As esters of fatty acids and glucose or alkylglucose, in particular glucose palmitate, alkylglucose sesquistearates such as methylglucose sesquistearate, alkylglucose palmitates such as methylglucose or ethylglucose palmitate, methylglucoside fatty esters and more specifically the diester of methylglucoside and oleic acid (Methyl glucose dioleate), the mixed ester of methylglucoside and the mixture oleic acid/hydroxystearic acid (Methyl glucose dioleate/hydroxystearate), the ester of methylglucoside and isostearic acid (Methyl glucose isostearate), the ester of methylglucoside and lauric acid (Methyl glucose laurate), the mixture of monoester and diester of methylglucoside and isostearic acid (Methyl glucose sesqui-isostearate), the mixture of monoester and diester of methylglucoside and stearic acid (Methyl glucose sesquistearate) and in particular the product marketed under the name Glucate SS by Lubrizol, and a mixture thereof can be cited.

As ethoxylated ethers of fatty acids and glucose or alkylglucose, ethoxylated ethers of fatty acids and methylglucose, and in particular the polyethylene glycol ether of the diester of methylglucose and stearic acid with about 20 moles of ethylene oxide (PEG-20 methyl glucose distearate) such as the product marketed under the name GLUCAM E-20 DISTEARATE by Lubrizol, the polyethylene glycol ether of the mixture of monoester and diester of methylglucose and stearic acid with about 20 moles of ethylene oxide (PEG-20 methyl glucose sesquistearate) and in particular the product marketed under the name GLUCAMATE SSE-20 by Lubrizol, and a mixture thereof, can for example be cited.

As sucrose esters, saccharose palmito-stearate, saccharose stearate and saccharose monolaurate can for example be cited.

As sugar ethers, alkylpolyglucosides can be used, and for example decylglucoside such as the product marketed under the name MYDOL 10 by Kao Chemicals, the product marketed under the name PLATAREN 2000 by BASF, and the product marketed under the name ORAMIX NS 10 by Seppic, caprylyl/capryl glucoside such as the product marketed under the name ORAMIX CG 110 by Seppic or under the name LUTENSOL GD 70 by BASF, laurylglucoside such as the products marketed under the names PLANTAREN 1200 N and PLANTACARE 1200 by BASF, cocoglucoside such as the product marketed under the name PLANTACARE 818/UP by BASF, cetostearyl glucoside possibly mixed with cetostearyl alcohol, marketed for example under the name MONTANOV 68 by Seppic, under the name TEGO-CARE CG90 by Evonik, arachidyl glucoside, for example in the form of the mixture of arachidyl and behenyl alcohols and arachidyl glucoside marketed under the name MONTANOV 202 by Seppic, cocoylethylglucoside, for example in the form of the mixture (35/65) with cetyl and stearyl alcohols, marketed under the name MONTANOV 82 by Seppic, and a mixture thereof can in particular be cited.

Mixtures of glycerides of alkoxylated plant oils such as mixtures of ethoxylated (200 EO) palm and copra (7 EO) glycerides can also be cited.

The nonionic surfactant may be selected from the group consisting of PEG-7 glyceryl cocoate, PEG-20 methylglucoside sesquistearate, PEG-20 glyceryl tri-isostearate, PG-5 dioleate, PG-4 diisostearate, PG-10 isostearate, PEG-8 isostearate, and PEG-60 hydrogenated castor oil.

Mixtures of these oxyethylenated derivatives of fatty alcohols and of fatty esters may also be used.

In some case, the nonionic surfactant is a fatty alkanolamide. Non-limiting examples of fatty alkanolamides that may be used include cocamide MEA, cocamide DEA, soyamide DEA, lauramide DEA, oleamide MIPA, stearamide MEA, myristamide DEA, stearamide DEA, oleylamide DEA, tallowamide DEA lauramide MIPA, tallowamide MEA, isostearamide DEA, isostearamide MEA, and a mixture thereof.

In some cases, the nonionic surfactant is an oxyethylenated amide such as PEG-4 rapeseedamide.

Implementation of the present disclosure is provided by way of the following examples. The examples serve to illustrate the technology without being limiting in nature.

| Example 1 (Coloring Base Composition) | | |
|---|---|---|
| Function | INCI US Name | Concentration |
| Alkalizing Agents | AMMONIUM HYDROXIDE AND ETHANOLAMINE | 8.7 |
| Reducing Agent | AMMONIUM THIOLACTATE | 0.5 |
| Cationic Conditioning Polymer | POLYQUATERNIUM-6 | 1.4 |
| Water Soluble Solvents | DIPROPYLENE GLYCOL, HEXYLENE GLYCOL, PROPYLENE GLYCOL, AND/OR ETHANOL | 20.4 |
| Anionic Surfactant | LAURETH-5 CARBOXYLIC ACID | 4.5 |
| Nonionic Surfactants | OLEYL ALCOHOL, PEG-4 RAPESEEDAMIDE, DECETH-3, AND/OR POLOXAMER 338 | 8.9 |
| Conditioning Agent | GLYCERYL LAURYL ETHER | 7 |
| Colorant | OXIDATIVE DYE PRECURSOR(S) AND COUPLERS | <0.1 |
| Miscellaneous | FRAGRANCE, PRESERVATIVES, ANTIOXIDANTS, ETC. | <3 |
| Water | WATER | q.s 100% |

| Example 2 (Developer Composition) | | |
|---|---|---|
| | INCI US Name | Concentration |
| Oxidizing Agent | HYDROGEN PEROXIDE | 7.5 |
| Water-Soluble Solvent | GLYCERIN | 0.5 |
| Nonionic Surfactants | TRIDECETH-2 CARBOXAMIDE MEA, CETEARYL ALCOHOL, AND/OR CETEARETH-25 | 3.8 |
| Miscellaneous | CHELATING AGENT(S), STABILIZER(S), BUFFERING AGENT(S), ETC. | <0.2 |
| Water | WATER | 88.2 |

Example 3

Mix Ratio Testing

The coloring base composition of Example 1 and the developer composition of Example 2 were incorporated into a hair coloring device to be mixed and dispensed. The device included a cartridge comprising a chamber for the hair coloring base composition and a separate chamber for the developer composition. The device also included a pump, a mixing assembly, a brushead/dispenser, and a control assembly operable to control the pump for dispensing the hair coloring base composition and the developer composition from their respective chambers to the mixing assembly and out of the brushead/dispenser (from tines of the brushead). The device was intended to mix and dispense a 1:1 ratio of hair coloring base composition and developer composition, i.e., the active hair coloring composition to be dispensed from the device was to be formed by a 1:1 ratio of hair coloring base composition and developer composition. The device may be adjusted to mix different ratios, as needed, but for the purposes of this study the desired mixing ratio was 1:1.

The active hair coloring composition dispensed by the device was evaluated to determine the mix ratio. Comparative base compositions and developer compositions were separately incorporated into the hair coloring device and the mix ratio of the resulting comparative active hair coloring compositions evaluated. The comparative compositions were commercially available hair coloring base compositions and developer compositions that required a mixing ratio of 1:1 according to the products' instructions. The results of the study are presented graphically in FIG. 1.

FIG. 1 shows that the device dispensed an active hair coloring composition having a 1:1 ratio of the hair coloring compositions of Example 1 and the developer composition of Example 2, as intended. Although the comparative compositions were also intended to be mixed and dispensed in a 1:1 ratio, such a result was not obtained with the comparative compositions. Instead, the comparative compositions dispensed by the device lacked sufficient amounts of hair coloring base composition (included too much developer composition).

The foregoing description illustrates and describes the disclosure. Additionally, the disclosure shows and describes only the preferred embodiments but, as mentioned above, it is to be understood that it is capable to use in various other combinations, modifications, and environments and is capable of changes or modifications within the scope of the invention concepts as expressed herein, commensurate with the above teachings and/or the skill or knowledge of the relevant art. The embodiments described herein above are further intended to explain best modes known by applicant and to enable others skilled in the art to utilize the disclosure in such, or other, embodiments and with the various modifications required by the particular applications or uses thereof. Accordingly, the description is not intended to limit the invention to the form disclosed herein. Also, it is intended to the appended claims be construed to include alternative embodiments.

As used herein, the terms "comprising," "having," and "including" are used in their open, non-limiting sense.

The terms "a," "an," and "the" are understood to encompass the plural as well as the singular. Thus, the term "a mixture thereof" also relates to "mixtures thereof." Throughout the disclosure, the term "a mixture thereof" is used, following a list of elements as shown in the following example where letters A-F represent the elements: "one or more elements selected from the group consisting of A, B, C, D, E, F, and a mixture thereof." The term, "a mixture thereof" does not require that the mixture include all of A, B, C, D, E, and F (although all of A, B, C, D, E, and F may be included). Rather, it indicates that a mixture of any two or more of A, B, C, D, E, and F can be included. In other words, it is equivalent to the phrase "one or more elements selected from the group consisting of A, B, C, D, E, F, and a mixture of any two or more of A, B, C, D, E, and F."

Likewise, the term "a salt thereof" also relates to "salts thereof." Thus, where the disclosure refers to "an element selected from the group consisting of A, B, C, D, E, F, a salt thereof, and a mixture thereof," it indicates that that one or more of A, B, C, D, and F may be included, one or more of a salt of A, a salt of B, a salt of C, a salt of D, a salt of E, and a salt of F may be include, or a mixture of any two of A, B, C, D, E, F, a salt of A, a salt of B, a salt of C, a salt of D, a salt of E, and a salt of F may be included.

The term "cartridge" as used herein refers to a modular unit holding a supply of material (e.g., a hair coloring base composition and a developer composition), the modular unit designed to be inserted into or connected with a device, appliance or piece of equipment.

The expression "one or more" means "at least one" and thus includes individual components as well as mixtures/combinations.

Other than in the operating examples, or where otherwise indicated, all numbers expressing quantities of ingredients and/or reaction conditions may be modified in all instances by the term "about," meaning within +/−5% of the indicated number.

Some of the various categories of components identified may overlap. In such cases where overlap may exist and the composition includes both components (or the composition includes more than two components that overlap), an overlapping compound does not represent more than one component. For example, a fatty acid may be considered both an emulsifier and a fatty compound. If a particular composition includes both an emulsifier and a fatty compound, a single fatty acid will serve as only the emulsifier or only the fatty compound (the single fatty acid does not serve as both the emulsifier and the fatty component).

The salts referred to throughout the disclosure may include salts having a counter-ion such as an alkali metal, alkaline earth metal, or ammonium counter-ion. This list of counter-ions, however, is non-limiting.

The term "treat" (and its grammatical variations) as used herein refers to the application of the compositions of the present disclosure onto the surface of keratinous substrates such as hair. The term 'treat' (and its grammatical variations) as used herein also refers to contacting keratinous substrates such as hair with the compositions of the present disclosure.

As used herein, all ranges provided are meant to include every specific range within, and combination of sub ranges between, the given ranges. Thus, a range from 1-5, includes specifically 1, 2, 3, 4 and 5, as well as sub ranges such as 2-5, 3-5, 2-3, 2-4, 1-4, etc. All ranges and values disclosed herein are inclusive and combinable. For examples, any value or point described herein that falls within a range described herein can serve as a minimum or maximum value to derive a sub-range, etc.

The term "substantially free" or "essentially free" as used herein means that there is less than about 2% by weight of a specific material added to a composition, based on the total weight of the compositions. Nonetheless, the compositions may include less than about 1 wt. %, less than about 0.5 wt. %, less than about 0.1 wt. %, or none of the specified material. All of the components set forth herein may be optionally included or excluded from the compositions/method/kits. When excluded, the compositions/methods/kits may be free or essentially free of the component. For example, a particular composition may be free or essentially free of alkoxylated compounds, for example, ethoxylated thickeners and/or ethoxylated surfactants. Likewise, a particular composition may be free or essentially free of sulfates, such as sulfate surfactants.

All publications and patent applications cited in this specification are herein incorporated by reference, and for any and all purposes, as if each individual publication or patent application were specifically and individually indicated to be incorporated by reference. In the event of an inconsistency between the present disclosure and any publications or patent application incorporated herein by reference, the present disclosure controls.

What is claimed is:

1. A hair color cartridge comprising:
    (a) one or more hair coloring base compositions comprising:
        one or more oxidative dye precursors;
        one or more alkalizing agents;
        one or more reducing agents;
        optionally, one or more cationic conditioning polymers;
        one or more surfactants;
        one or more water-soluble solvents; and
        water;
            wherein the viscosity of each of the one or more hair coloring base compositions is about 25 to about 150 cps at 25° C. using a #1 spindle at 100 rpm; and
    (b) one or more developer compositions comprising:
        one or more oxidizing agents;
        one or more surfactants;
        water;
            wherein the viscosity of each of the one or more developer compositions is about 250 to about 2000 cps at 25° C. using a #4 spindle at 100 rpm;
        wherein each hair coloring base composition and each developer composition are separately contained until use; and
        wherein the cartridge is configured for use with a hair coloring device via a portal member for receiving or attaching to the cartridge.

2. The hair color cartridge of claim 1, wherein the one or more hair coloring base compositions comprise one or more oxidative dye precursors selected from the group consisting of ortho- and/or para-aminophenols, ortho- and/or para-phenylenediamines, double bases, heterocyclic bases, acid addition salts thereof, and a mixture thereof.

3. The hair color cartridge of claim 1, wherein the total amount of the one or more oxidative dye precursors is about 0.001 to about 5 wt. %, based on the total weight of the hair coloring base composition.

4. The hair color cartridge of claim 1, wherein the one or more hair coloring base compositions comprise one or more alkalizing agents selected from the group consisting of ammonium hydroxide, monoethanolamine, sodium silicate, sodium metasilicate, and a mixture thereof.

5. The hair color cartridge of claim 1, wherein each hair coloring base composition comprises about 1 to about 25 wt. % of the one or more alkalizing agents, based on the total weight of the hair coloring base composition.

6. The hair color cartridge of claim 1, wherein the one or more hair coloring base compositions comprise one or more reducing agents selected from the group consisting of ammonium bisulfite, ammonium sulfite, potassium metabisulfite, potassium sulfite, sodium hydrosulfite, sodium metabisulfite, sodium sulfite, sodium bisulphite, thioglycolic acid, thiolactic acid, dehydroascorbic acid, a salt thereof, and a mixture thereof.

7. The hair color cartridge of claim 1, wherein each of the hair coloring base compositions comprises about 0.01 to about 5 wt. % of the one or more reducing agents, based on the total weight of the hair coloring base composition.

8. The hair color cartridge of claim 1, wherein the one or more hair coloring base compositions comprise one or more cationic conditioning polymers selected from the group consisting of polyquaterniums.

9. The hair color cartridge of claim 8, wherein the one or more hair coloring base compositions comprise about 0.1 to about 10 wt. % of the one or more cationic conditioning polymers, based on the total weight of the hair coloring base composition.

10. The hair color cartridge of claim 1, wherein the one or more hair coloring base compositions comprise one or more anionic surfactants, one or more nonionic surfactants, or a combination thereof.

11. The hair color cartridge of claim 10, wherein the one or more hair coloring base compositions comprise one or more anionic surfactants and one or more nonionic surfactants.

12. The hair color cartridge of claim 1, wherein each hair coloring base composition comprises about 1 to about 35 wt. % of the one or more surfactants, based on the total weight of the hair coloring base composition.

13. The hair color assembly of claim 1, wherein the one or more hair coloring base compositions comprise one or more water-soluble solvents selected from the group consisting of glycerin, alcohols, organic solvents, polyols, glycols, and a mixture thereof.

14. The hair color cartridge of claim 1, wherein each hair coloring base composition comprises about 1 to about 45 wt. % of the one or more water-soluble solvents, based on the total weight of the hair coloring base composition.

15. The hair color cartridge of claim 1, wherein each hair coloring base composition comprises about 5 to about 60 wt. % of water, based on the total weight of the hair coloring base composition.

16. The hair color cartridge of claim 1, wherein the one or more hair coloring base compositions comprise:
- about 0.001 to about 5 wt. % of one or more oxidative dye precursors selected from the group consisting of ortho- and/or para-aminophenols, ortho- and/or para-phenylenediamines, double bases, heterocyclic bases, acid addition salts thereof, and a mixture thereof;
- about 1 to about 25 wt. % of one or more alkalizing agents selected from the group consisting of ammonium hydroxide, monoethanolamine, sodium silicate, sodium metasilicate, and a mixture thereof;
- about 0.01 to about 5 wt. % of one or more reducing agents selected from the group consisting of ammonium bisulfite, ammonium sulfite, potassium metabisulfite, potassium sulfite, sodium hydrosulfite, sodium metabisulfite, sodium sulfite, sodium bisulphite, thioglycolic acid, thiolactic acid, dehydroascorbic acid, a salt thereof, and a mixture thereof;
- about 0.1 to about 10 wt. % of one or more cationic conditioning polymers selected from the group consisting of polyquaterniums;
- about 1 to about 35 wt. % of one or more surfactants;
- about 1 to about 45 wt. % of one or more water-soluble solvents selected from the group consisting of glycerin, alcohols, organic solvents, polyols, glycols, and a mixture thereof; and
- about 5 to about 60 wt. % of water;
  wherein the weight percentages are based on the total weight of an individual hair coloring base composition.

17. The hair color cartridge of claim 1, wherein the one or more developer compositions comprise one or more oxidizing agents selected from the group consisting of hydrogen peroxide, inorganic alkali metal peroxides, organic peroxides, inorganic perhydrate salts, bromates, and a mixture thereof.

18. The hair color cartridge of claim 1, wherein each developer composition comprises about 1 to about 40 wt. % of the one or more oxidizing agents, based on the total weight of the developer composition.

19. The hair color cartridge of claim 1, wherein the one or more developer compositions comprise one or more nonionic surfactants.

20. The hair color cartridge of claim 1, wherein each developer composition comprises about 0.1 to about 20 wt. % of the one or more surfactants, based on the total weight of the developer composition.

* * * * *